United States Patent
Verlee et al.

(10) Patent No.: US 8,001,926 B2
(45) Date of Patent: *Aug. 23, 2011

(54) SYSTEM AND METHOD OF LOADING AND DETECTING BENEFICIAL AGENT ON A PROSTHESIS

(75) Inventors: Donald Verlee, Libertyville, IL (US); Peter Tarcha, Lake Villa, IL (US); Keith Cromack, Gurnee, IL (US); Richard Quint, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/551,413

(22) Filed: Aug. 31, 2009

(65) Prior Publication Data
US 2010/0003396 A1    Jan. 7, 2010

Related U.S. Application Data

(62) Division of application No. 11/465,396, filed on Aug. 17, 2006, now Pat. No. 7,597,764, which is a division of application No. 10/703,820, filed on Nov. 7, 2003, now Pat. No. 7,208,190.

(60) Provisional application No. 60/424,574, filed on Nov. 7, 2002, provisional application No. 60/424,575, filed on Nov. 7, 2002, provisional application No. 60/424,576, filed on Nov. 7, 2002, provisional application No. 60/424,577, filed on Nov. 7, 2002, provisional application No. 60/424,607, filed on Nov. 7, 2002.

(51) Int. Cl.
*B05C 11/00* (2006.01)
*B05B 3/00* (2006.01)

(52) U.S. Cl. ........ 118/712; 118/669; 118/665; 118/321; 118/323; 118/679

(58) Field of Classification Search .................. 118/500, 118/503, 320, 504, 505, 325, 306, 317, 665, 118/688, 696, 697, 712, 713, 300, 695, 620–640, 118/668, 669, 321, 323, 679; 427/2.1, 2.24, 427/256, 8; 623/1.13, 1.11, 194, 1.46, 1.47, 623/1.48; 606/192, 198

See application file for complete search history.

(56) References Cited

U.S. PATENT DOCUMENTS
4,324,812 A * 4/1982 Bentley .............................. 427/8
(Continued)

FOREIGN PATENT DOCUMENTS
DE    19940241    8/1999
(Continued)

OTHER PUBLICATIONS

Cooley, et al., "Applications of Ink-Jet Printing Technology to BioMEMS and Microfluidic Systems". Proc. SPIE Conf. on Micreofluidics, Oct. 2001.

*Primary Examiner* — Yewebdar T Tadesse
(74) *Attorney, Agent, or Firm* — Squire, Sanders & Dempsey (US) LLP

(57) ABSTRACT

An interventional device for delivery of beneficial agent to a lumen and methods of loading and manufacture of the same, which include a prosthesis loaded with beneficial agent to provide a controlled dosage concentration of beneficial agent to the lumen. The beneficial agent is loaded onto the prosthesis by a fluid-dispenser having a dispensing element capable of dispensing the beneficial agent in discrete droplets, each droplet having a controlled trajectory. The method of loading beneficial agent includes dispensing beneficial agent in a raster format and/or an off-axis format along a dispensing path.

16 Claims, 11 Drawing Sheets

U.S. PATENT DOCUMENTS

Figure 1A:
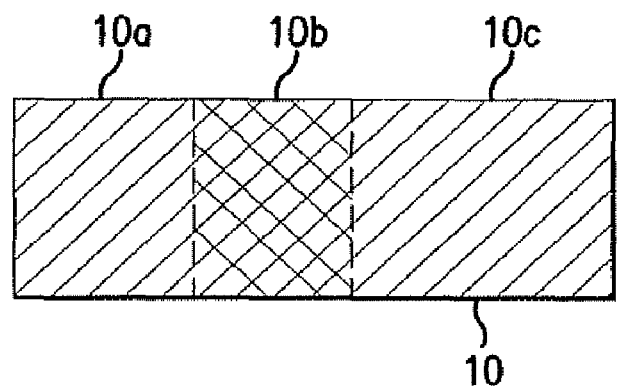

| | | | |
|---|---|---|---|
| 4,877,745 A | 10/1989 | Hayes et al. | |
| 5,464,650 A | 11/1995 | Berg et al. | |
| 5,591,227 A | 1/1997 | Dinh et al. | |
| 5,605,696 A | 2/1997 | Eury et al. | |
| 5,644,391 A * | 7/1997 | Grego et al. | 356/128 |
| 5,649,977 A | 7/1997 | Campbell | |
| 5,667,840 A | 9/1997 | Tingey et al. | |
| 5,741,429 A | 4/1998 | Donadio et al. | |
| 5,820,918 A | 10/1998 | Ronan et al. | |
| 5,824,048 A | 10/1998 | Tuch | |
| 5,824,049 A | 10/1998 | Ragheb et al. | |
| 5,837,313 A | 11/1998 | Ding et al. | |
| 5,873,904 A | 2/1999 | Ragheb et al. | |
| 5,906,682 A | 5/1999 | Bouras et al. | |
| 5,951,586 A | 9/1999 | Berg et al. | |
| 5,980,972 A | 11/1999 | Ding | |
| 6,027,863 A | 2/2000 | Donadio, III | |
| 6,033,434 A | 3/2000 | Borghi | |
| 6,086,942 A | 7/2000 | Carden, Jr. et al. | |
| 6,096,070 A | 8/2000 | Ragheb et al. | |
| 6,099,562 A | 8/2000 | Ding et al. | |
| 6,107,004 A | 8/2000 | Donadio, III | |
| 6,121,027 A | 9/2000 | Clapper et al. | |
| 6,153,252 A | 11/2000 | Hossainy et al. | |
| 6,187,322 B1 | 2/2001 | Hille et al. | |
| 6,209,621 B1 | 4/2001 | Treacy | |
| 6,231,600 B1 | 5/2001 | Zhong | |
| 6,251,136 B1 | 6/2001 | Guruwaiya et al. | |
| 6,254,634 B1 | 7/2001 | Anderson et al. | |
| 6,273,913 B1 | 8/2001 | Wright et al. | |
| 6,287,332 B1 | 9/2001 | Bolz et al. | |
| 6,296,708 B1 * | 10/2001 | Coulibaly et al. | 118/679 |
| 6,299,604 B1 | 10/2001 | Ragheb et al. | |
| 6,319,277 B1 | 11/2001 | Rudnick et al. | |
| 6,335,029 B1 | 1/2002 | Ramath et al. | |
| 6,358,556 B1 | 3/2002 | Ding et al. | |
| 6,379,379 B1 | 4/2002 | Wang | |
| 6,387,121 B1 | 5/2002 | Alt | |
| 6,395,326 B1 | 5/2002 | Castro et al. | |
| 6,409,716 B1 | 6/2002 | Sahatjian et al. | |
| 6,506,437 B1 | 1/2003 | Harish et al. | |
| 6,558,733 B1 | 5/2003 | Hossainy et al. | |
| 6,616,765 B1 | 9/2003 | Wu et al. | |
| 6,645,547 B1 | 11/2003 | Shekalim et al. | |
| 6,676,987 B2 | 1/2004 | Zhong et al. | |
| 6,713,119 B2 | 3/2004 | Hossainy et al. | |
| 6,743,463 B2 | 6/2004 | Weber et al. | |
| 6,808,536 B2 | 10/2004 | Wright et al. | |
| 6,901,659 B1 * | 6/2005 | Mishima | 29/846 |
| 7,048,962 B2 | 5/2006 | Shekalim et al. | |
| 7,208,190 B2 | 4/2007 | Verlee et al. | |
| 7,597,764 B2 * | 10/2009 | Verlee et al. | 118/667 |
| 2002/0051846 A1 | 5/2002 | Kirkpatrick et al. | |
| 2003/0068355 A1 | 4/2003 | Shanley et al. | |
| 2003/0083646 A1 | 5/2003 | Sirhan et al. | |
| 2003/0207019 A1 | 11/2003 | Shekalim et al. | |
| 2004/0130584 A1 | 7/2004 | Kobayashi et al. | |
| 2004/0185081 A1 | 9/2004 | Verlee et al. | |
| 2004/0254634 A1 | 12/2004 | Verlee et al. | |
| 2005/0158449 A1 * | 7/2005 | Chappa | 427/2.1 |
| 2007/0189915 A1 | 8/2007 | Shirvastava et al. | |
| 2007/0191943 A1 | 8/2007 | Shrivastava et al. | |
| 2008/0020129 A1 | 1/2008 | Verlee et al. | |

FOREIGN PATENT DOCUMENTS

| | | |
|---|---|---|
| DE | 19940242 | 8/1999 |
| EP | 0850651 | 12/1997 |
| WO | WO 98/01107 | 1/1998 |
| WO | WO 98/32474 | 7/1998 |
| WO | WO 01/03625 | 10/2001 |
| WO | WO 01/91918 | 12/2001 |
| WO | WO 02/069848 | 9/2002 |
| WO | WO 2004/043298 | 5/2004 |
| WO | WO 2004/043299 | 5/2004 |
| WO | WO 2004/043300 | 5/2004 |

* cited by examiner

SYSTEM AND METHOD OF LOADING AND DETECTING BENEFICIAL AGENT ON A PROSTHESIS

CROSS-REFERENCE TO RELATED APPLICATIONS

This application is a divisional of application Ser. No. 11/465,396 filed Aug. 17, 2006, now U.S. Pat. No. 7,597,764 which is a divisional of application Ser. No. 10/703,820, filed Nov. 7, 2003, now U.S. Pat. No. 7,208,190, which claims the benefit of Provisional Application Nos. 60/424,574; 60/424,575; 60/424,576; 60/424,577; and 60/424,607, each of the provisional applications filed on Nov. 7, 2002. Each of the above-identified applications are incorporated herein by reference.

BACKGROUND OF THE INVENTION

1. Field of the Invention

The invention relates to a method and system for loading beneficial agent onto a prosthesis using a fluid-dispenser having a dispensing element capable of dispensing beneficial agent in discrete droplets, each droplet having a controlled trajectory. The method in particular relates to a method of dispensing beneficial agent in a raster format and/or an off-axis format along a dispensing path.

2. Description of Related Art

Percutaneous transluminal coronary angioplasty (PTCA) is a procedure for treating heart disease. This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

While PCTA is widely used, it suffers from two unique problems. First, the blood vessel may suffer acute occlusion immediately after or within the initial hours after the dilation procedure. Such occlusion is referred to as "abrupt closure." Abrupt closure occurs in approximately five percent of cases in which PTCA is employed. The primary mechanisms of abrupt closures are believed to be elastic recoil, arterial dissection and/or thrombosis. The second problem associated with this procedure is the re-narrowing of an artery after an initially successful angioplasty. This re-narrowing is referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce occlusion of the artery, and the development of thrombosis and/or restenosis, an expandable interventional device or prosthesis, one example of which includes a stent, is implanted in the lumen to maintain the vascular patency. Additionally, to better effectuate the treatment of such vascular disease, it is preferable to load an intraluminal device or prosthesis with one or more beneficial agents, such as anti-proliferatives, for delivery to a lumen. One commonly applied technique for the local delivery of a drug is through the use of a polymeric carrier coated onto the surface of a stent, as disclosed in Berg et al., U.S. Pat. No. 5,464,650, the disclosure of which is incorporated herein by reference thereto. Such conventional methods and products generally have been considered satisfactory for their intended purpose. However, some problems associated with such drug eluting interventional devices is the variability in drug loading across an interventional device, as well as the variability in drug concentration from device to device. Other disadvantages include the inability to tightly control and maintain drug concentration, the inability to verify drug distribution or drug loading on any given device, the inability to vary drug distribution in a controlled and predetermined manner to effect a more desirable drug loading profile, the inability to load different, and in particular incompatible or reactive drugs onto the same surface of a device, and the difficulty in controlling the local areal density of beneficial agent that is delivered to the lumen, particularly if the interventional device is an overlapping or bifurcated device coated with beneficial agent.

As evident from the related art, conventional methods of loading interventional devices with beneficial agents, such as drugs, often requires coating the entire prosthesis with a polymer capable of releasing therapeutic drugs, as disclosed in Campbell, U.S. Pat. No. 5,649,977 and Dinh et al., U.S. Pat. No. 5,591,227, the disclosures of which are incorporated herein by reference thereto. Because certain interventional devices may have a varied surface area along its length, such conventional loading techniques results in unintentional or undesirable dosage variations. Additionally, if it is desired to superimpose two or more conventional-loaded prostheses, such as with nested stents or bifurcated stents, the total dosage of beneficial agent to the lumen will exceed the nominal or desired dosage. Another drawback of the conventional methods of loading interventional devices with beneficial agents is the lack of selective dosing, such as providing various beneficial agents or various concentrations of the same beneficial agent at different locations on a prosthesis to effect a therapy at specific targeted sites.

Thus, there remains a need for efficient and economic methods for controlling the loading of beneficial agent onto a prosthesis so as to provide an interventional device having a varied distribution profile of beneficial agent to effect therapy at targeted locations of the lumen. Additionally, there is a need for an interventional device capable of providing combination therapy of two or more beneficial agents loaded on different surfaces of a prosthesis to effectuate systemic release as well as release to the wall of the lumen. Further, a need exists for the loading of incompatible beneficial agents onto the same surface of a prosthesis. The advantages of the present invention satisfy the aforementioned needs.

SUMMARY OF THE INVENTION

The purpose and advantages of the present invention will be set forth in and will become apparent from the description that follows, as well as will be learned by practice of the invention.

Additionally, advantages of the invention will be realized and attained by the methods and systems particularly pointed out in the written description and claims hereof, as well as from the appended drawings.

In aspects of the present invention, a system for loading beneficial agent onto a prosthesis for delivery within a lumen comprises a holder, a fluid-dispenser, a driver, a controller, and a beneficial agent detector. The holder is for supporting a prosthesis to be deployed within a lumen. The fluid-dispenser has a dispensing element capable of dispensing beneficial agent in discrete droplets, each droplet having a controlled trajectory, the dispensing element and the holder being movable relative to each other, said dispensing element being positioned at a distance sufficient such that the dispensing element and prosthesis in the holder are separated by a distance that avoids simultaneous contact of the dispensing element and prosthesis by a discrete droplet. The driver is for creating relative movement between the dispensing element and the holder. The controller is in communication with the driver to define a dispensing path for dispensing discrete droplets of beneficial agent with the controlled trajectory in a raster format, the controller is also in communication with the dispensing element to selectively dispense beneficial agent from the dispensing element to a predetermined portion of a prosthesis supported by the holder along the dispensing path. The beneficial agent detector is in communication with the controller configured to determine an amount of beneficial agent loaded on a prosthesis, the beneficial agent detector being configured to be capable of detecting charge build-up on or current flow from the prosthesis to determine a corresponding amount of beneficial agent loaded to the prosthesis.

In other aspects, the controlled trajectory is controlled by the controller so as to not intersect a central axis of the prosthesis.

In other aspects, the beneficial agent detector is configured to be capable of detecting the number of discrete droplets dispensed from the fluid-dispenser onto the prosthesis to determine a corresponding amount of beneficial agent loaded to the prosthesis.

In aspects of the present invention, a method for loading beneficial agent onto a prosthesis for delivery within a lumen comprising supporting on a holder a prosthesis to be deployed within a lumen. The method further comprises dispensing from a dispensing element a beneficial agent in discrete droplets, each droplet having a controlled trajectory. The method further comprises positioning the dispensing element at a distance from the holder, the distance sufficient to avoid simultaneous contact of the dispensing element and prosthesis by the dispensed discrete droplets. The method further comprises moving the holder and the dispensing element relative to each other, the movement defining a dispensing path for the dispensing of the discrete droplets of the beneficial agent with the controlled trajectory in a raster format. The method further comprises determining an amount of the beneficial agent dispensed on the prosthesis.

In further aspects, the determining of the amount of the beneficial agent dispensed on the prosthesis includes detecting a charge build-up on or current flow from the prosthesis.

In further aspects, the determining of the amount of the beneficial agent dispensed on the prosthesis includes detecting the number of discrete droplets dispensed from the dispensing element onto the prosthesis.

In further aspects, the controlled trajectory does not intersect a central axis of the prosthesis.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

FIGS. 1*a*-1*c* are schematic representations of a prosthesis loaded with beneficial agent having a first portion and a second portion having different local areal densities of beneficial agent in accordance with the present invention, and graphs depicting corresponding areal density.

FIG. 2 is a schematic representation of a first prosthesis and a second prosthesis configured to define a nested interventional device, each at least partially loaded with beneficial agent in accordance with the present invention.

FIG. 3 is a schematic representation of the first prosthesis and second prosthesis of FIG. 2, deployed in overlapping relationship to provide a controlled local areal density across the length of the interventional device.

FIG. 4 is a schematic representation of a first prosthesis and second prosthesis configured to define a bifurcated interventional device, each at least partially loaded with beneficial agent in accordance with the present invention.

FIG. 5 is a schematic representation of the first prosthesis and second prosthesis of FIG. 4, deployed in an overlapping relationship to provide a bifurcated interventional device having a controlled local areal density across a length of the interventional device.

FIG. 6 is a schematic representation of an interventional device, and FIG. 6*a* is a detail schematic depicting a raster format for loading beneficial agent thereon.

FIG. 7 is a schematic representation of an embodiment of the system of the present invention.

FIGS. 8*a*-8*d* are schematic representations of an “off-axis” dispensing method at various cross-sections of the device of FIG. 6.

FIG. 9 is a schematic representation of another embodiment of the system of the present invention.

FIG. 10 is a schematic representation of discrete droplets loaded in an overlapping manner.

FIG. 11 is a schematic representation of a method of loading beneficial agent on an inner surface of an interventional device.

FIG. 12 is a schematic representation of the cross-section of the structural element of a prosthesis having a cavity therein.

FIG. 13 is a schematic representation of the holding tool assembly of the system of the invention, FIG. 13*a* is a detail schematic depicting the holding tool assembly including the spindle.

DETAILED DESCRIPTION OF THE EMBODIMENTS

Reference will now be made in detail to the present preferred embodiments of the method and system for loading beneficial agent onto a prosthesis, and the interventional devices loaded with beneficial agent. Wherever possible, the same reference characters will be used throughout the drawings to refer to the same or like parts.

In accordance with the present invention, an interventional device is provided for delivery of beneficial agent within a lumen. Particularly, the present invention is suited for providing an interventional device having a controlled areal density of beneficial agent for the treatment and prevention of vascular or other intraluminal diseases. Generally, “controlled areal density” is understood to mean a known or predetermined amount of beneficial agent, either by weight or volume, over a unit surface area of the interventional device.

As used herein “interventional device” refers broadly to any device suitable for intraluminal delivery or implantation. For purposes of illustration and not limitation, examples of such interventional devices include stents, grafts, stent-grafts, filters, and the like. As is known in the art, such devices may comprise one or more prostheses, each having a first cross-sectional dimension or profile for the purpose of delivery and a second cross-sectional dimension or profile after deployment. Each prosthesis may be deployed by known mechanical techniques such as balloon expansion deployment techniques, or by electrical or thermal actuation, or self-expansion deployment techniques, as well known in the art. Examples of such for purpose of illustration include U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, all of which are incorporated herein by reference.

For purposes of explanation and illustration, and not limitation, an exemplary embodiment of the interventional device in accordance with the invention is shown schematically in FIG. 1a. In accordance with one aspect of the invention, as shown schematically in FIG. 1, the interventional device generally includes a prosthesis 10 loaded with beneficial agent to provide a local areal density of beneficial agent across a length of the interventional device. Particularly, as embodied herein the prosthesis may be a stent, a graft, a stent-graft, a filter, or the like, as previously noted, for intravascular or coronary delivery and/or implantation. However, the prosthesis may be any type of intraluminal member capable of being loaded with beneficial agent.

The prosthesis can be in an expanded or unexpanded state during the loading of beneficial agent. The underlying structure of the prosthesis can be virtually any structural design and the prosthesis can be composed any suitable material such as, but not limited to, stainless steel, "MP35N," "MP20N," elastinite (Nitinol), tantalum, nickel-titanium alloy, platinum-iridium alloy, gold, magnesium, polymer, ceramic, tissue, or combinations thereof "MP35N" and "MP20N" are understood to be trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium and 10% molybdenum. The prosthesis can be made from bioabsorbable or biostable polymers. In some embodiments, the surface of the prosthesis can include one or more reservoirs or cavities formed therein, as described further below.

The prosthesis can be fabricated utilizing any number of methods known in the art. For example, the prosthesis can be fabricated from a hollow or formed tube that is machined using lasers, electric discharge milling, chemical etching or other known techniques. Alternatively, the prosthesis can be fabricated from a sheet that is rolled into a tubular member, or formed of a wire or filament construction as known in the art.

As noted above, the prosthesis is at least partially loaded with beneficial agent (10a, 10b, 10c). "Beneficial agent" as used herein, refers to any compound, mixture of compounds, or composition of matter consisting of a compound, which produces a beneficial or useful result. The beneficial agent can be a polymer, a marker, such as a radiopaque dye or particles, or can be a drug, including pharmaceutical and therapeutic agents, or an agent including inorganic or organic drugs without limitation. The agent or drug can be in various forms such as uncharged molecules, components of molecular complexes, pharmacologically-acceptable salts such as hydrochloride, hydrobromide, sulfate, laurate, palmitate, phosphate, nitrate, borate, acetate, maleate, tartrate, oleate, and salicylate.

An agent or drug that is water insoluble can be used in a form that is a water-soluble derivative thereof to effectively serve as a solute, and on its release from the device, is converted by enzymes, hydrolyzed by body pH, or metabolic processes to a biologically active form. Additionally, the agents or drug formulations can have various known forms such as solutions, dispersions, pastes, particles, granules, emulsions, suspensions and powders. The drug or agent may or may not be mixed with polymer or a solvent as desired.

For purposes of illustration and not limitation, the drug or agent can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors. Other drugs or agents include but are not limited to antineoplastics, antimitotics, antifibrins, antioxidants, agents that promote endothelial cell recovery, anti-allergic substances, radiopaque agents, viral vectors, antisense compounds, oligionucleotides, cell permeation enhancers, angiogenesis agents, and combinations thereof.

Examples of such antithrombotics, anticoagulants, antiplatelet agents, and thrombolytics include sodium heparin, low molecular weight heparins, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as ANGIOMAX™, from Biogen, Inc., Cambridge, Mass.; and thrombolytic agents, such as urokinase, e.g., ABBOKINASE™ from Abbott Laboratories Inc., North Chicago, Ill., recombinant urokinase and pro-urokinase from Abbott Laboratories Inc., tissue plasminogen activator (ALTEPLASE™ from Genentech, South San Francisco, Calif. and tenecteplase (TNK-tPA).

Examples of such cytostatic or antiproliferative agents include rapamycin and its analogs such as everolimus, ABT-578, i.e., 3S,6R,7E,9R,10R,12R,14S,15E,17E,19E,21S,23S,26R,27R,34aS)-9,10,12,13,14,21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone; 23,27-Epoxy-3H pyrido [2,1-c][1,4]oxaazacyclohentriacontine-1,5,11,28,29(4H,6H,31H)-pentone, which is disclosed in U.S. Pat. No. 6,015,815, U.S. Pat. No. 6,329,386, US Publication 2003/129215, filed on Sep. 6, 2002, and US Publication 2002/123505, filed Sep. 10, 2001, the disclosures of which are each incorporated herein by reference thereto, tacrolimus and pimecrolimus, angiopeptin, angiotensin converting enzyme inhibitors such as captopril, e.g., CAPOTEN® and CAPOZIDE® from Bristol-Myers Squibb Co., Stamford, Conn., cilazapril or lisinopril, e.g., PRINIVIL® and PRINZIDE® from Merck & Co., Inc., Whitehouse Station, N.J.; calcium channel blockers such as nifedipine, amlodipine, cilnidipine, lercanidipine, benidipinie, trifluperazine, diltiazem and verapamil, fibroblast growth factor antagonists, fish oil (omega 3-fatty acid), histamine antagonists, lovastatin, e.g. MEVACOR® from Merck & Co., Inc., Whitehouse Station, N.J. In addition, topoisomerase inhibitors such as etoposide and topotecan, as well as antiestrogens such as tamoxifen may be used.

Examples of such anti-inflammatories include colchicine and glucocorticoids such as betamethasone, cortisone, dexamethasone, budesonide, prednisolone, methylprednisolone and hydrocortisone. Non-steroidal anti-inflammatory agents include flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of such antineoplastics include alkylating agents such as altretamine, bendamucine, carboplatin, carmustine, cisplatin, cyclophosphamide, fotemustine, ifosfamide, lomustine, nimustine, prednimustine, and treosulfin, antimitotics such as vincristine, vinblastine, paclitaxel, e.g., TAXOL® by Bristol-Myers Squibb Co., Stamford, Conn., docetaxel, e.g., TAXOTERE® from Aventis S.A., Frankfort, Germany, antimetabolites such as methotrexate, mercaptopurine, pentostatin, trimetrexate, gemcitabine, azathioprine, and fluorouracil, and antibiotics such as doxorubicin hydrochloride, e.g., ADRIAMYCIN® from Pharmacia & Upjohn, Peapack, N.J., and mitomycin, e.g., MUTAMYCIN® from Bristol-Myers Squibb Co., Stamford, Conn., agents that promote endothelial cell recovery such as Estradiol.

Additional drugs which may be utilized in this application include dexamethasone; fenofibrate; inhibitors of tyrosine kinase such as RPR-101511A; PPAR-alpha agonists such as TRICOR™ formulation from Abbott Laboratories Inc., North Chicago, Ill.; endothelin receptor antagonists such as ABT-627 having general formula $C_{29}H_{38}N_2O_6 \cdot ClH$, and the following structural formula

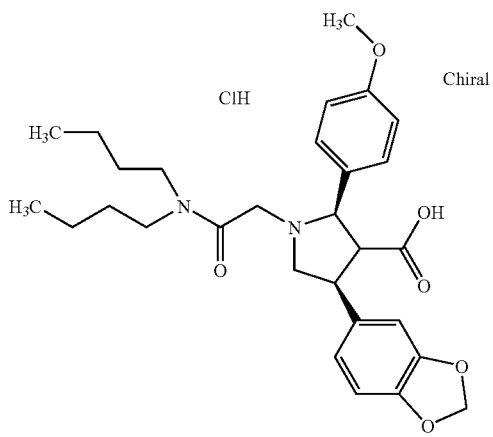

from Abbott Laboratories Inc., North Chicago, Ill., as disclosed in U.S. Pat. No. 5,767,144, the disclosure of which is incorporated herein by reference; matrix metalloproteinase inhibitors such as ABT-518 {[S—(R*,R*)]-N-[1-(2,2-dimethyl-1,3-dioxol-4-yl)-2-[[4-[4-(trifluoro-methoxy)-phenoxy]phenyl]sulfonyl]ethyl]-N-hydroxyformamide}, having general formula $C_{21}H_{22}F_3NO_8S$ and having the following structural formula

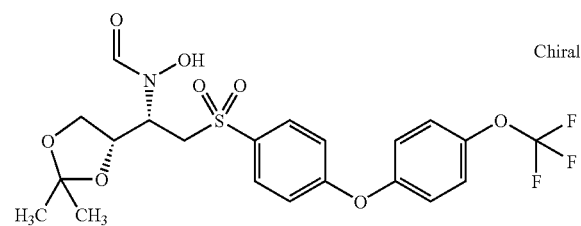

from Abbott Laboratories Inc., North Chicago, Ill., which is disclosed in U.S. Pat. No. 6,235,786, the disclosure of which is incorporated herein by reference; ABT 620 {1-Methyl-N-(3,4,5-trimethoxyphenyl)-1H-indole-5-sulfonamide}, which is disclosed in U.S. Pat. No. 6,521,658, the disclosure of which is incorporated herein by reference; antiallergic agents such as permirolast potassium nitroprusside, phosphodiesterase inhibitors, prostaglandin inhibitors, suramin, serotonin blockers, steroids, thioprotease inhibitors, triazolopyrimidine, and nitric oxide.

While the foregoing beneficial agents are known for their preventive and treatment properties, the substances or agents are provided by way of example and are not meant to be limiting. Further, other beneficial agents that are currently available or may be developed are equally applicable for use with the present invention.

If desired or necessary, the beneficial agent can include a binder to carry, load, or allow sustained release of an agent, such as but not limited to a suitable polymer or similar carrier. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable.

For purpose of illustration and not limitation, the polymeric material include phosphorylcholine linked macromolecules, such as a macromolecule containing pendant phosphorylcholine groups such as poly($MPC_w$:$LMA_x$:$HPMA_y$:$TSMA_z$), where MPC is 2-methacryoyloxyethylphosphorylcholine, LMA is lauryl methacrylate, HPMA is hydroxypropyl methacrylate and TSMA is trimethoxysilylpropyl methacrylate, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, PARYLENE®, PARYLAST®, polyurethane including polycarbonate urethanes, polyethylene, polyethylene terapthalate, ethylene vinyl acetate, ethylene vinyl alcohol, silicone including polysiloxanes and substituted polysiloxanes, polyethylene oxide, polybutylene terepthalate-co-PEG, PCL-co-PEG, PLA-co-PEG, polyacrylates, polyvinyl pyrrolidone, polyacrylamide, and combinations thereof. Non-limiting examples of other suitable polymers include thermoplastic elastomers in general, polyolefin clastomers, EPDM rubbers and polyamide elastomers, and biostable plastic material such as acrylic polymers, and its derivatives, nylon, polyesters and epoxies. Preferably, the polymer contains pendant phosphoryl groups as disclosed in U.S. Pat. Nos. 5,705,583 and 6,090,901 to Bowers et al. and U.S. Pat. No. 6,083,257 to Taylor et al., which are all incorporated herein by reference.

The beneficial agent can include a solvent. The solvent can be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof. Preferably, the solvent is ethanol. More preferably, the solvent is isobutanol. Additionally, in another aspect of the invention, multiple beneficial agents are dissolved or dispersed in the same solvent. For purpose of illustration and not for limitation, dexamethasone, estradiol, and paclitaxel are dissolved in isobutanol. Alternatively, dexamethasone, estradiol, and paclitaxel are dissolved in ethanol. In yet another example, dexamethasone, estradiol, and ABT-578, i.e., the rapamycin analog, 3S,6R,7E,9R,10R,12R,14S, 15E,17E,19E,21 S,23S,26R,27R,34aS)-9,10,12,13,14,21, 22,23,24,25,26,27,32,33,34,34a-Hexadecahydro-9,27- dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone; 23,27-Epoxy-3H-pyrido[2,1-c][1,4]oxaazacyclohentriacontine-1,5,11,28,29(4H,6H,3H)-pentone, are dissolved together in one solvent. Preferably, the solvent is ethanol. More preferably, the solvent is isobutanol.

Additionally, the beneficial agent includes any of the aforementioned drugs, agents, polymers, and solvents either alone or in combination.

A number of methods can be used to load the beneficial agent onto the surface of the prosthesis to provide for a controlled local areal density of beneficial agent if performed appropriately. For example, the prosthesis can be constructed to include pores or reservoirs which are impregnated or filled with beneficial agent or multiple beneficial agents. The pores can be sized or spaced apart to correspond to or limit the amount of beneficial agent contained therein in accordance with the desired local areal density pattern along the length of the interventional device, wherein larger pores or more dense spacing would be provided in such portions intended to have a greater local areal density. Alternatively, uniform pores sizes can be provided but the amount of beneficial agent loaded therein is limited accordingly. Additionally, if desired, a membrane of biocompatible material can then be applied over the pores or reservoirs for sustained or controlled release of the beneficial agent from the pores or reservoirs.

According to some of the embodiments, the beneficial agent can be loaded directly onto the prosthesis or alternatively, the beneficial agent is loaded onto a base material layer that is applied to a surface of the prosthesis. For example and not limitation, a base coating, such as a binder or suitable polymer, is applied to a selected surface of the prosthesis such that a desired pattern is formed on the prosthesis surface. Beneficial agent is then applied directly to the pattern of the base material.

In one aspect of the invention, the desired pattern corresponds to the desired controlled local areal density. For example, a greater amount of base material layer is applied to portions of the interventional device intended to have a greater local areal density of beneficial agent, and a lesser amount of base material is applied to portions of the interventional device intended to have a lower local areal density of beneficial agent.

Alternatively, a suitable base coating capable of retaining beneficial agent therein can be applied uniformly over the surface of the prosthesis, and then selected portions of the base coating can be loaded with the beneficial agent in accordance with the invention. A greater amount of beneficial agent would be loaded over a unit surface area of the base coating intended to have a greater local areal density and a lower amount of beneficial agent would be loaded over a unit surface area intended to have a lower local areal density.

In yet another embodiment of the present invention, the beneficial agent can be applied directly to the surface of the prosthesis. Generally a binder or similar component can be required to ensure sufficient adhesion. For example, this coating technique can include admixing the beneficial agent with a suitable binder or polymer to form a coating mixture, which is then coated onto the surface of the prosthesis. The coating mixture is prepared in higher or lower concentrations of beneficial agent as desired, and then applied to selected portions of the prosthesis appropriately.

In any of the embodiments disclosed herein, a porous or biodegradable membrane or layer made of biocompatible material can be coated over the beneficial agent for sustained release thereof, if desired.

Conventional coating techniques can be utilized to coat the beneficial agent onto the surface of the prosthesis such as spraying, dipping or sputtering and still provide the desired effect if performed appropriately. With such techniques, it may be desirable or necessary to use known masking or extraction techniques to control the location and amount in which beneficial agent is loaded. Prior to coating the prosthesis with beneficial agent, optical machine vision inspection of the prosthesis preferably is utilized to ensure that no mechanical defects exist. Defective prostheses thus can be rejected before wasting beneficial agent, some of which may be very costly.

In accordance with one aspect of the invention, however, the beneficial agent is "printed" onto the surface of the prosthesis by a fluid-dispenser having a dispensing element capable of dispensing beneficial agent in discrete droplets, wherein each droplet has a controlled trajectory. If desired, printing can be combined with conventional coating techniques such as spraying or dipping.

"Fluid-dispenser," as used herein, refers broadly to any device having a dispensing element capable of dispensing fluid in discrete droplets wherein each droplet has a controlled trajectory. For purposes of illustration and not limitation, examples of such fluid-dispensers include fluid-jetting and similar fluid dispensing technology devices such as a drop-on-demand fluid printer and a charge-and-deflect fluid printer. However, other fluid-dispensers capable of forming a fluid jet or capable of dispensing discrete droplets having a controlled trajectory are within the scope of the present invention. In a preferred embodiment, the fluid-dispenser is a fluid-jet print head. Such equipment is available from MicroFab Technologies of Plano, Tex.

Fluid-jetting and similar technology provides numerous advantages not available with conventional loading techniques. For example, fluid jetting technology can be used to deposit materials, such as chemical reagents, in controlled volumes onto a substrate at a controlled location, as disclosed in U.S. Pat. No. 4,877,745 to Hayes et al., incorporated herein by reference.

Fluid jetting can also be used to deposit materials in a reproducible way. Fluid-jet based deposition of materials is data driven, non-contact, and requires no tooling. The "printing" information can be created directly from CAD information and stored digitally in software or hardware. Thus, no masks or screens are required. As an additive process with no chemical waste, fluid-jetting is environmentally friendly. Other advantages include the efficiency of fluid jet printing technology. For example, fluid-jetting can dispense spheres of fluid with diameters of 15-200 um at rates of 1-25,000 per second for single droplets on demand, and up to 1 MHz for continuous droplets. See Cooley et al., "Applications of Ink-Jet Printing Technology to BioMEMS and Microfluidic Systems," *Proc. SPIE Conf. on Microfluidics*, (October 2001), incorporated herein by reference.

In accordance with one aspect of the invention, a method of loading beneficial agent onto a prosthesis for delivery within a lumen is disclosed. The method comprises the steps of providing a prosthesis, beneficial agent to be delivered from the prosthesis, and a fluid-dispenser having a dispensing element capable of dispensing the beneficial agent in discrete droplets, wherein each droplet has a controlled trajectory. The method further includes creating relative movement between the dispensing element and the prosthesis to define a dispensing path and selectively dispensing the beneficial agent in a raster format to a predetermined portion of the prosthesis along the dispensing path. In particular, the beneficial agent is selectively dispensed from the dispensing element to a predetermined portion of the prosthesis in a raster format along a dispensing path. As used herein "raster format" refers to a continuous or non-continuous dispensing pattern of droplets of beneficial agent dispensed at specific intervals. The relative motion of the dispensing element and the prosthesis to be loaded with beneficial agent creates a dispensing path which includes, for example and as shown in FIG. 6a, a sequential series of linear parallel passes 154 that traverse back and forth along one axis of the prosthesis. The relative motion is continued in a linear manner between forward and backward or right to left and left to right or upward and downward, depending on the frame of reference. A traversal or a pass 154 is completed when the relative motion reverses direction. That is, relative motion continues past the prosthesis, and then decelerates, stops, reverses direction and accelerates to a constant velocity. After each pass, the position of the dispensing element 150 or prosthesis 10 relative to the dispensing element preferably is changed or incremented such that additional droplets do not impact in the same location during the subsequent pass, although a certain degree of overlap may be permitted. For example, as the dispensing element dispenses the beneficial agent along the prosthesis, a fluid dispensing width "w" is defined. The dispensing path defined by the relative movement between the dispensing element and the prosthesis can include a series of parallel passes wherein each parallel pass has a path width no greater than the fluid dispensing width defined by the dispensing element, although a greater path width can be defined if desired.

Figure 10:
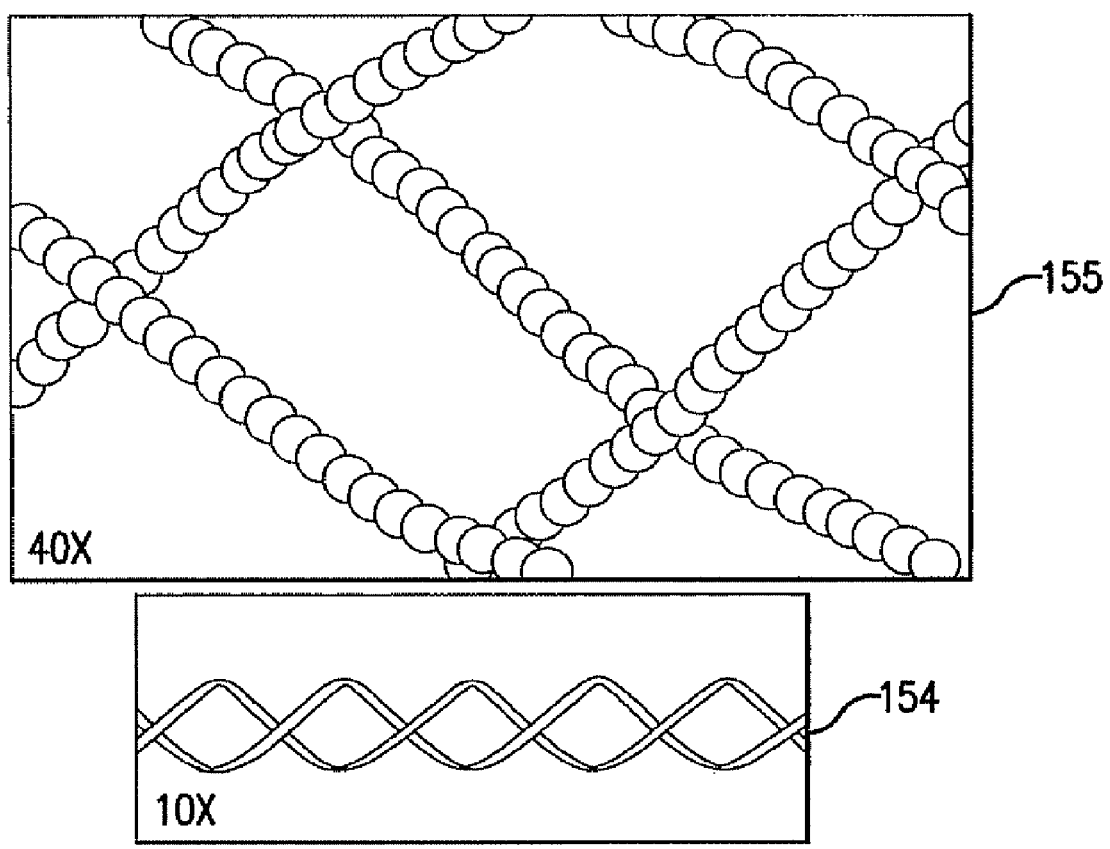

Alternatively, the dispensing path created by the relative motion of the dispensing element 150 and the prosthesis 10 can include a single continuous helix that wraps continuously around the prosthesis tubular body and along the length of the prosthesis. FIG. 10 schematically depicts such a helical path. In this manner, selectively fluid dispensing in a raster format similar to that of the linear paths previously described can be performed using a helical path if desired. In a preferred embodiment, the direction of travel of relative motion consists of continuously rotating, for example, the prosthesis 10 to be loaded and then incrementally advancing the dispensing element axially along the prosthesis. Both axial and radial motion preferably begin before the prosthesis 10 is aligned with the dispensing element 150 to receive droplets, so as to enable acceleration of both axes to a constant velocity, and continues beyond the prosthesis where both movements may decelerate, and stop. After each rotation, the position of the dispensing element 150 or of the prosthesis 10 relative to the dispensing element is moved or incremented axially such that additional droplets of beneficial agent preferably do not impact in the same location, Any degree of overlap may be permitted to achieve the desired areal density of beneficial agent.

Figure 6:
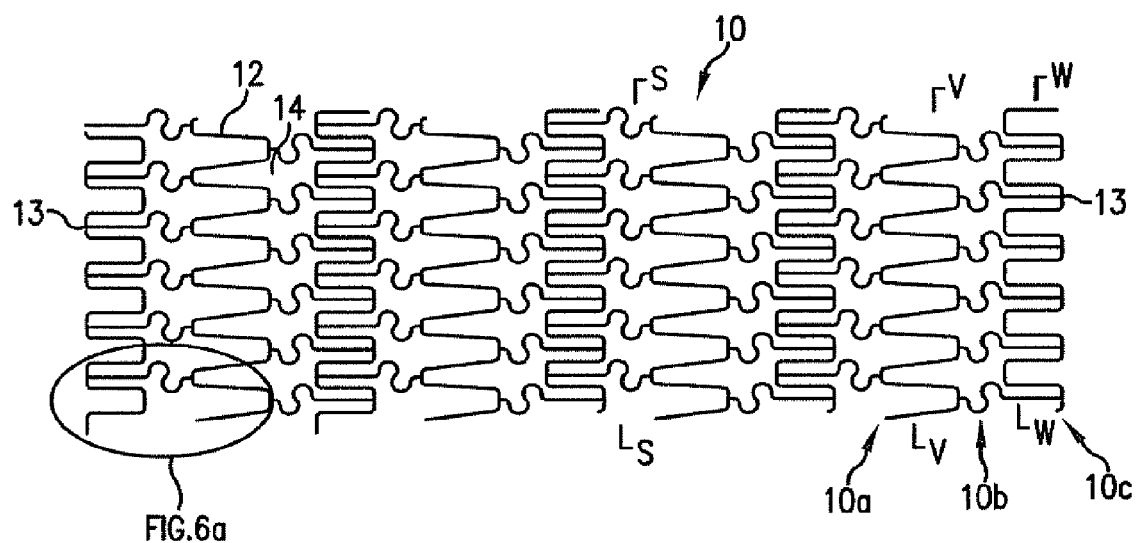
Figure 6A:
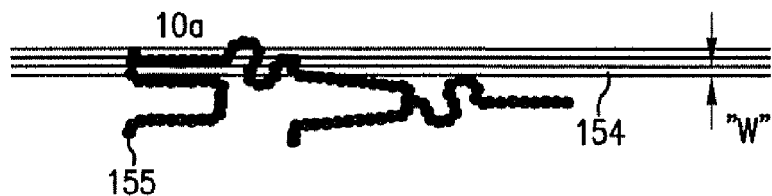
Figure 7:
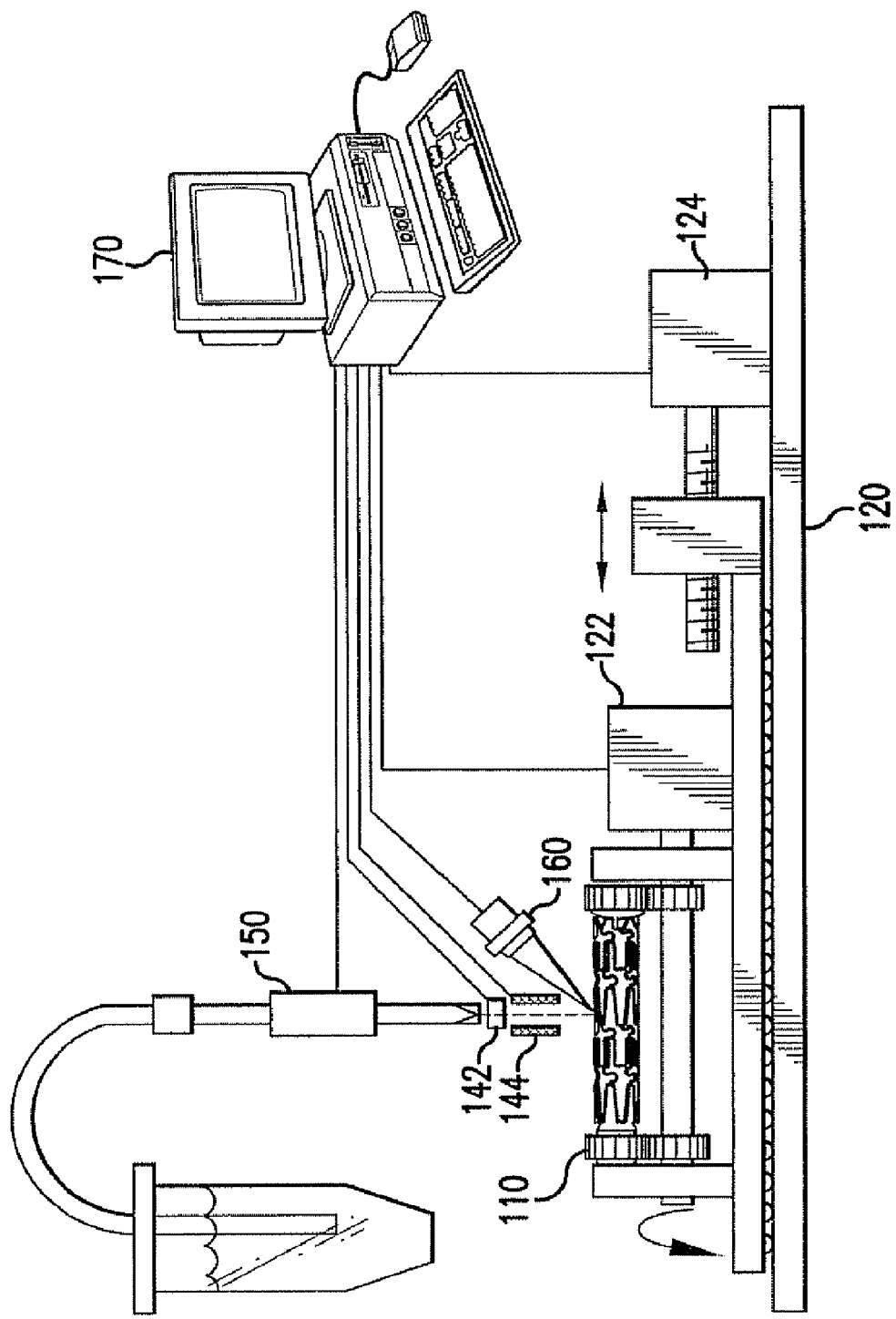
Figure 8A:
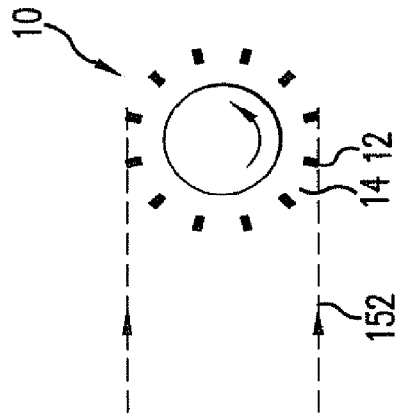
Figure 8B:
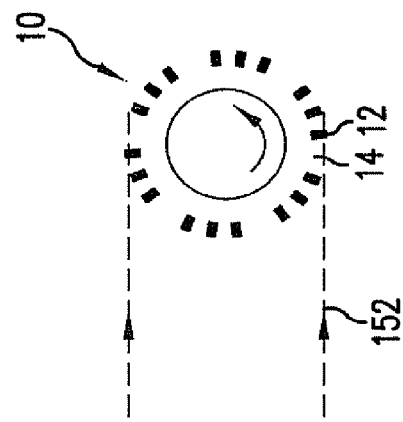
Figure 8C:
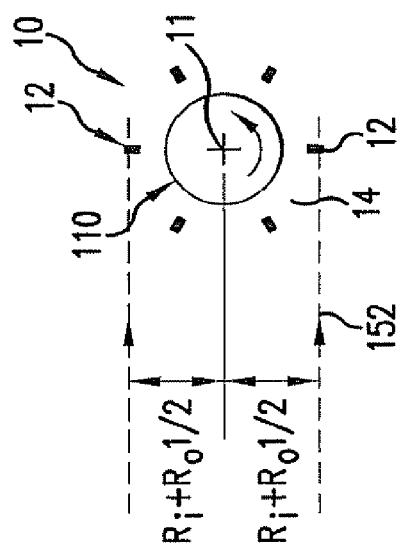
Figure 8D:
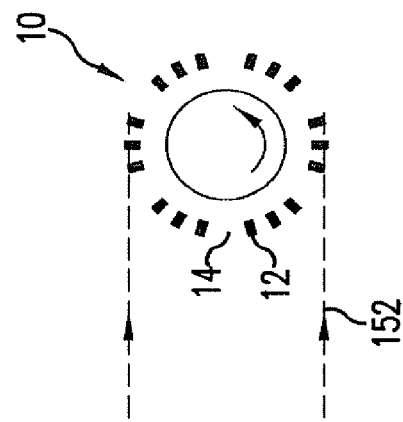

For purpose of illustration of this method, and as shown in FIGS. 6 and 7, the prosthesis 10 includes a plurality of interconnected structural members 12 defining openings 14 therebetween and the beneficial agent 15 is dispensed only when the dispensing element 150 and the structural members 12 within a predetermined portion of the prosthesis 10 are aligned with each other. Accordingly, in this preferred embodiment, dispensing beneficial agent 15 ceases when the dispensing element 150 and the structural members 12 of the prosthesis are not in alignment. To this end, the method can include a detecting step to determine when the dispensing element 150 is aligned with the structural members 12 of a prosthesis 10. The detecting step can be achieved by a sensor 160 such as an optical detector, e.g., linear array detector or infrared detector, ultrasound probe, temperature probe, camera, capacitance meter, electrometer, hall-effect probe, and the like. However, any sensor 160 known in the art for detection is within the scope of the invention. Alternatively, a controller 170 may be provided that is programmed with the structural member locations of a predetermined portion of the prosthesis to be loaded with beneficial agent. In this manner, the dispensing step is performed by the dispensing element as operated by the programmed controller. These aspects of the invention reduce or eliminate webbing and bridging of beneficial agent across openings or gaps within the structure of the prosthesis and minimizes waste. Furthermore, the dispensing element 150 can be aligned such that the controlled trajectory of each droplet is directed normal to the surface of the prosthesis, or at an angle thereto. Similarly, the trajectory path can be aligned to cross the central axis of the prosthesis, or be aligned off-axis thereto.

According to another aspect of the invention, the method of loading beneficial agent onto the prosthesis includes providing a prosthesis including a tubular member having a central axis defined along a length of the tubular member. This method further includes dispensing beneficial agent from a dispensing element capable of dispensing beneficial agent in discrete droplets and in a controlled trajectory to a surface of the prosthesis, wherein the controlled trajectory of beneficial agent is aligned so as not to intersect the central axis of the tubular member.

For example, and for purpose of illustration and not limitation, FIGS. 8a-8d depict various cross-sections of the interventional device 10 of FIG. 6. In each cross-sectional view, the trajectory path 152 of the discrete droplets 155 is aligned "off-axis" so as not to pass through the central axis 11 of the tubular member. Particularly, and as depicted in FIGS. 8a through 8d for purpose of illustration and not limitation, the trajectory path 152 of the discrete droplets 155 is aligned tangentially between an inner surface and an outer surface of the tubular wall of the prosthesis 10. In this manner, likelihood of impact of a discrete droplet 155 of beneficial agent 15 with a surface of the prosthesis 11 is enhanced. If desired, however, alternative off-axis trajectory path alignment can be used in accordance with the invention.

With reference to FIGS. 8a-8d, the prosthesis provided by the prosthesis providing step includes a tubular member having a plurality of interconnected structural members 12 defining openings 14 therebetween, and further wherein the controlled trajectory 152 of each droplet is substantially tangential to a wall or surface of the structural members 12 within the predetermined portion of the prosthesis. In this regard, the controlled trajectory 152 of beneficial agent 15 dispensed from the dispensing element 150 is aligned such that it does not intersect the central axis of the prosthesis. This process allows for greater coverage of the structural elements, without requiring selective operation of the dispensing element, if desired. That is, use of the "off-axis" approach allows for enhanced loading of beneficial agent on the prosthesis without selective or with only limited control of the dispensing element if desired. In a preferred embodiment, however, the dispensing element is at least controlled to terminate dispensing when the trajectory path is not aligned with the solid profile of the predetermined area to be loaded, e.g. axially beyond either end 13 of the prosthesis 10, shown in FIG. 6. In particular, the dispensing element is turned "on" only when the trajectory path of beneficial agent will intersect the solid area swept out by 360 degrees rotation of the prosthesis. The dispensing element is turned off when the trajectory path of beneficial agent would not intersect or will miss the solid area and volume swept out by 360 degrees rotation of the prosthesis.

Alternatively, and in accordance with a preferred embodiment of the invention, the "off-axis" method is performed using the raster technique previously described. That is, with the trajectory path 152 aligned off-axis from the central axis of the prosthesis 10, such as shown in FIGS. 8a-8d, discrete droplets can be selectively dispensed from the dispensing element 150 only when aligned with a structural member 12 of the prosthesis 10. In this embodiment, the relative motion of the dispensing element 150 and the prosthesis 10 define a dispensing path which includes a sequential series of linear parallel passes that traverse back and forth along one axis of the prosthesis. The relative motion alternates between forward and backward, right to left, left to right, or upward and downward, depending on the frame of reference. A traversal or pass is completed when the relative motion changes direction. That is, relative motion continues past the prosthesis and then decelerates, stops, reversed direction and accelerates to a constant velocity. After each pass, the position of the dispensing element 150 is changed or incremented such that additional drops of beneficial agent do not impact the same location as the previously dispensed droplets during the subsequent pass. Any degree of overlap may be permitted to achieve a desired areal density of beneficial agent.

Alternatively, the relative motion of the dispensing element and the prosthesis define a dispensing path which includes a single continuous helix that wraps around the prosthesis and along its length. The relative motion consists of continuously rotating, for example, the prosthesis and then incrementally advancing the dispensing element 150 axially along the prosthesis. Both axial and radial motion preferably begin before the item is aligned with the dispensing element to receive droplets of beneficial agent, so as to enable acceleration of both axes to a constant velocity, and continues beyond the prosthesis where both movements may decelerate, and stop. After each rotation, the position of the dispensing element or prosthesis relative to the dispensing element is moved or incremented axially such that additional droplets preferably do not impact in the same location. However, any degree of overlap may be permitted to achieve a desired areal density of beneficial agent.

The linear velocity during dispensing of droplets of beneficial agent can be constant or can be varied in a controlled way. Further, the preferable position of the droplet trajectory is such that the droplets interact with the structural surfaces of the prosthesis at or near the tangent to its curved solid surface.

In a preferred embodiment the dispensing path 154 includes a series of parallel passes along a surface of the prosthesis. For example and not limitation, the prosthesis provided can have a tubular body prior to its deployment in a lumen, and each parallel pass of the dispensing path 154 is parallel to the longitudinal axis 11 of the prosthesis 10 as shown in FIG. 6a. After each pass, the position of the dispensing element 150 or prosthesis 10 is changed or incremented so that the discrete droplets 155 of beneficial agent 15 are dispensed onto a surface of the prosthesis 10 that has not already been loaded. Alternatively, and as previously noted, the parallel passes can define a helical pattern around the longitudinal axis of the stent, wherein each pass is a complete turn of the helical pattern. For purposes of illustration and not limitation, the relative motion of the dispensing element and the prosthesis can include continuously rotating the prosthesis and incrementally advancing the dispensing element axially along the length of the prosthesis. Preferably, after each rotation of the prosthesis, the position of the dispensing element is incrementally changed axially such that additional droplets of beneficial agent that are dispensed from the dispensing element load a surface of the prosthesis not already loaded by a prior pass. In an alternative aspect of the invention, the prosthesis can have a planar body prior loading, such that no rotation of the planar member is required for loading of beneficial agent thereon. The step of dispensing the beneficial agent onto the prosthesis along the dispensing path can be repeated to provide multiple passes along a predetermined portion of the prosthesis.

Figure 9:
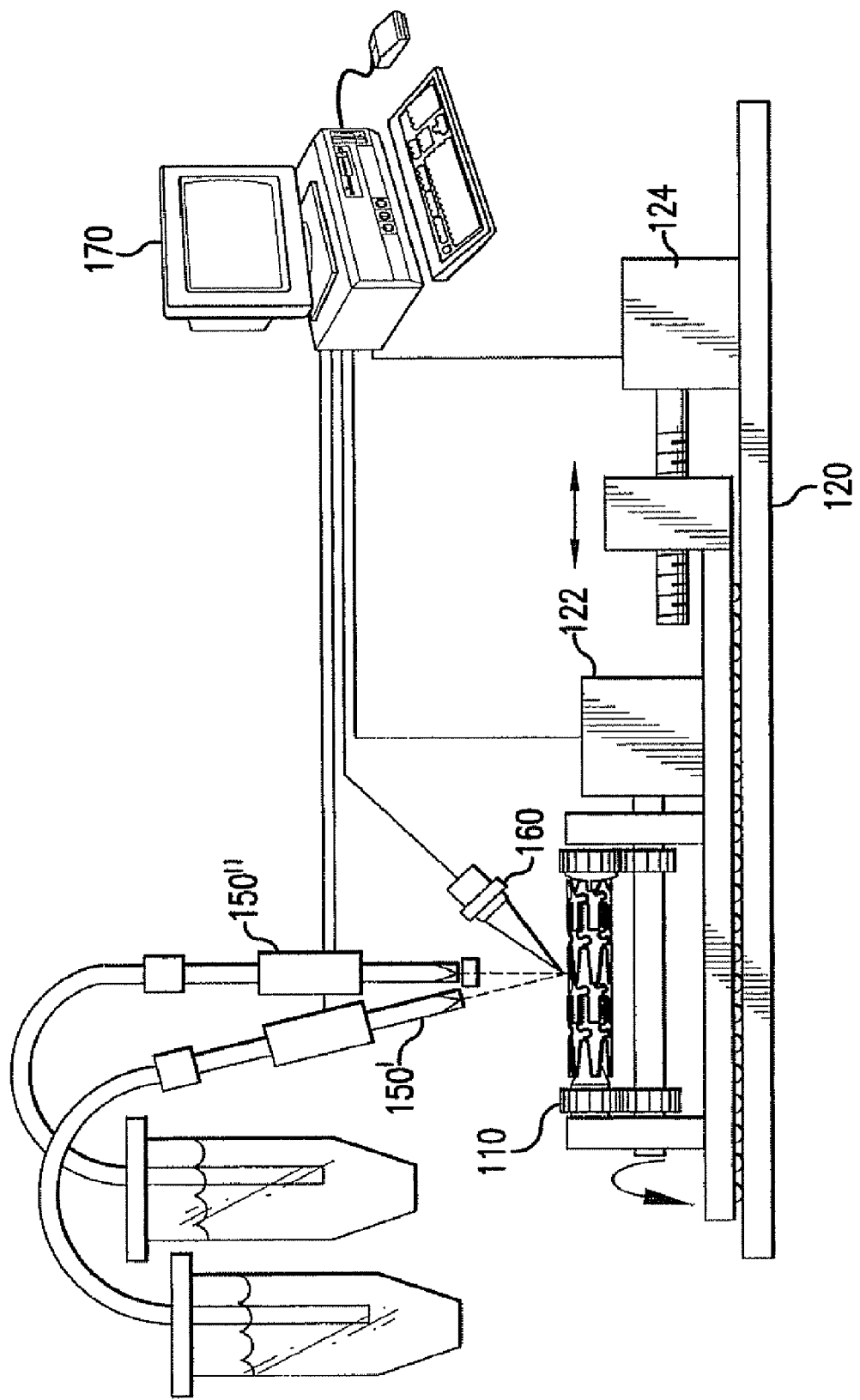
Figure 11:
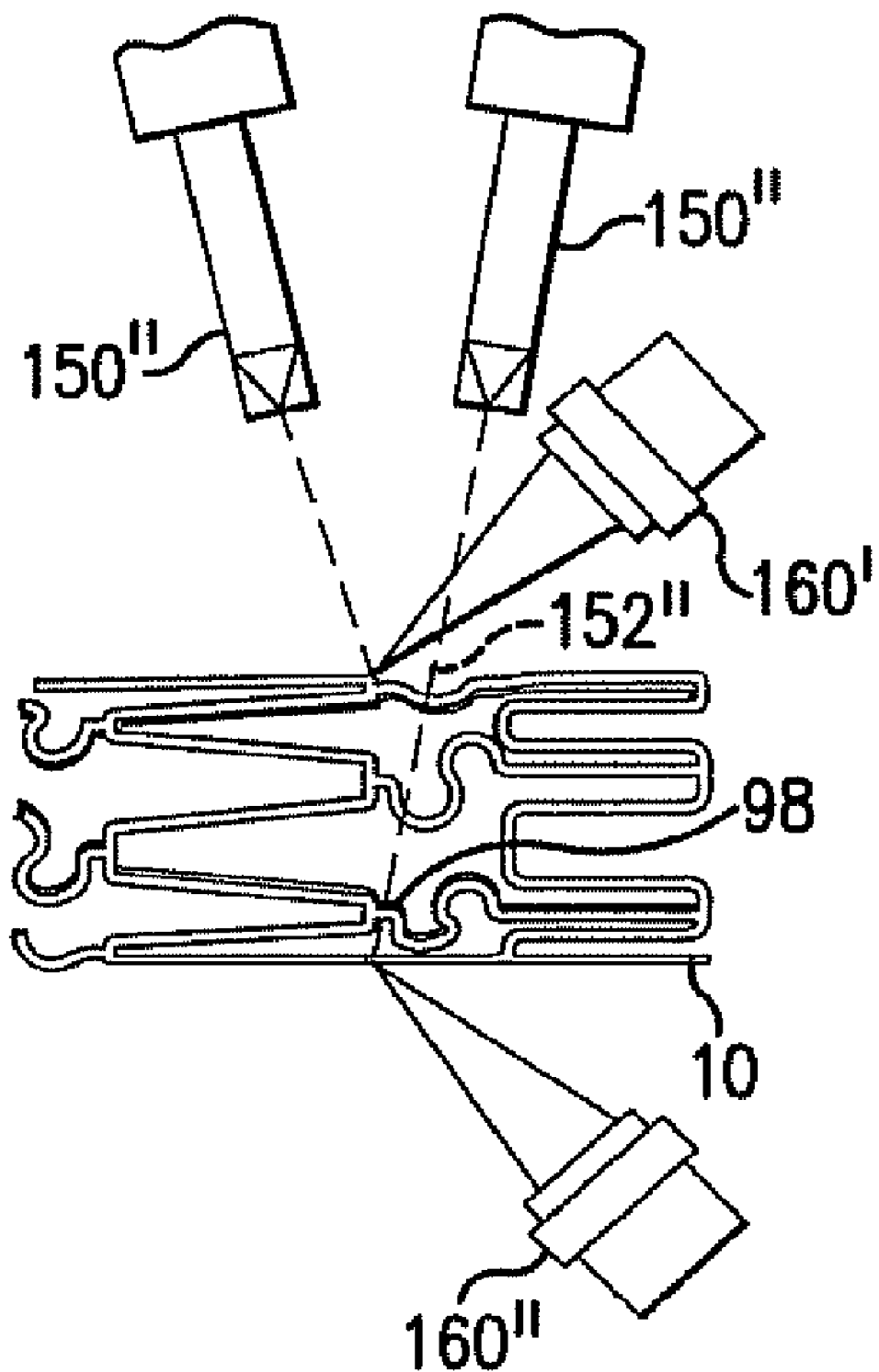

As noted above, the beneficial agent is selectively dispensed from the dispensing element along the dispensing path in a raster format. In this manner, the raster format can be achieved by turning the dispensing element on and off at predetermined intervals in response to a detector. Alternatively, the beneficial agent can be selectively dispensed in a raster format by programming a controller device that communicates with the dispensing element to dispense the beneficial agent according to the programmed data. A variety of fluid dispensers are available and suitable for providing discrete droplets along a controlled trajectory. For example, a suitable drop-on-demand jetting system can be used, as shown in FIGS. 9 and 11, wherein discrete droplets are selectively dispensed from a jetting head. In this manner, the jet stream of discrete droplets can be turned on and off on demand, and the flow rate of discrete droplets can be increased or decreased as desired. Alternatively, if a charge-and-deflect device is used, then a continuous stream of droplets will be generated, and selected droplets will be deflected as is known in the art, such as shown in FIG. 7, as described further below.

In an embodiment of the invention the prosthesis is a stent, and as mentioned above, the fluid-dispenser is a fluid-jetting device. In accordance with the preferred embodiment, a driver 120 continually advances the stent longitudinally along its axis at a constant rate, to define a series of generally parallel passes 154 along the longitudinal axis 11 of the stent 10. The stent is the incrementally rotated about its axis at the end of each pass. The stent is rotated at about 1 degree to about 20 degrees about its longitudinal axis, increments, and preferably is rotated at about 5 degree increments.

The fluid-jetting head is turned on to provide droplets of beneficial agent whenever a stent strut or structural member is detected immediately in front of the jetting head, or based on a predetermined programmed pattern that corresponds to the stent design, as mentioned above. By further providing controlled flow rate dispensed from the jetting head, the beneficial agent can be provided in a rastered format to confer the stent with a known quantity of beneficial agent. If desired, the known quantity of beneficial agent is dispensed to provide a uniform local areal density based on changes in surface area. As used herein "local areal density" refers to the amount of beneficial agent per unit surface area of the stent or prosthesis.

For example and not limitation, a unit length of two different struts having different strut widths could each be loaded with an equal amount of beneficial agent by adjusting flow rate accordingly. Contrastly, the flow rate of the jetting head can be controlled along the progression of the stent to provide a first portion 10b of the prosthesis 10 with a greater local areal density and a second portion 10a of the prosthesis with a lower local areal density, such as shown in FIG. 1. Similarly, the rate of relative movement between the jetting head and the prosthesis can be varied to control local areal density accordingly.

As noted above, the dispensing path 154 is defined by the relative movement between the dispensing element and the prosthesis. The relative movement between the dispensing element and the prosthesis may be performed at a substantially constant velocity, or alternatively at a varied velocity to alter local areal density of beneficial agent, or intermittently. For an example of varied velocity, and with reference to the embodiment of FIG. 1a for purpose of illustration and not limitation, the linear travel speed of the prosthesis under the fluid dispenser is performed 50% faster during loading of beneficial agent on the proximal and distal portions 10a and 10c of the prosthesis body to decrease local areal density accordingly. Alternatively, the linear travel speed of the prosthesis under the fluid dispenser may be 50% slower during loading of beneficial agent on the mid region of the prosthesis body to increase local areal density thereat.

Alternatively, rather than using a raster format, a vector technique can be used wherein a first portion of the stent strut at one end of the stent is positioned in front of the jetting head and the jetting head is turned on. The jetting head is then left on to dispense droplets of beneficial agent at a constant predetermined frequency to provide a predetermined dispensing rate of agent. The two-axis control system, described further below, is directed to continuously move the stent, coordinating both axes simultaneously so that the predetermined shape of the stent struts are advanced in front of the jetting head. This movement continuously places the beneficial agent on the struts of the first portion until the desired surface of the stent has been positioned to receive beneficial agent over the known surface area, and a predetermined quantity of beneficial agent has been dispensed. The beneficial agent is provided on the stent struts and the jetting head thereby does not disperse beneficial agent in areas wherein metal has been removed from the stent. This process may be repeated for subsequent portions of the interventional device, such that known quantities of beneficial agent are provided over each corresponding portion of the interventional device. As with the raster format, flow rate or rate of relative movement can be controlled to adjust local areal density of beneficial agent as desired.

In yet another embodiment, the two-axis positioning system is coupled to a charge-and-deflect jetting head. A charge-and-deflect jetting head is capable of producing a rastered pattern of droplets over a predetermined width of the stent. That is, it is also in accordance with the invention to apply a surface charge to selected droplets of beneficial agent dispensed from the dispensing element. Preferably, if a positive surface charge is applied to the beneficial agent, an antioxidant can be included in the beneficial agent. In this manner, the antioxidant can help to prevent the oxidation of a beneficial agent that might otherwise oxidize when positively charged. Additionally, or alternatively, other known techniques can be used to prevent or inhibit oxidation of beneficial agent. The trajectory of charged droplets of beneficial agent can be altered by a deflection field. For example, an electrode 144 may be used to deflect the trajectory of beneficial agent, which is charged by a charger 142, towards a predetermined portion of the prosthesis as shown in FIG. 7. If desired, a charge opposite that induced on the droplets of beneficial agent can be applied to a predetermined portion of the prosthesis to provide an electrostatic attraction between the droplets of beneficial agent and the prosthesis for greater accuracy and efficiency.

To effect predetermined loading of beneficial agent, or coating thickness, several methods of controlling the two-axis positioning system in coordination with control of the fluid dispensing are possible so as to result in a precise deposition of beneficial agent on the outer surface of the stent or prosthesis 10. First, the motor 122 that controls rotation of the prosthesis about its longitudinal axis can be turned on to produce a constant angular velocity. A second motor 124 is then controlled to advance the prosthesis or stent in front of the dispensing element 150 at a predetermined rate to generally describe a spiral or helix across the longitudinal axis of the stent, where the pitch width, from rotation to rotation, is the same as the raster width of the dispensing element 150. When a charge-and-deflect dispensing element is used, the surface of the prosthesis 10 or stent can be exposed to the dispensing element 150 in a more rapid manner than for the single drop wide raster pattern that is possible with the drop-on-demand mode system. When the first stent strut is detected to be present in front of the jet head 150, a bit-mapped pattern that has been previously stored in memory 170 to describe the shape of the struts is rastered out by providing appropriate charges on selected droplets. Second, a linear array detector 160 with resolution similar to the number of droplets in each raster line can detect, by reflected or transmitted light, the presence of a stent strut that is about to revolve in front of the jetted fluid window. The data from this type of detector can then be transferred to a shift register which produces the necessary raster data by shifting the bit pattern out a bit at a time. With this method, no predetermined bit-map is necessary, and any slight variations in speed, edge detection or position may be automatically compensated. This process may be repeated for subsequent portions of the interventional device, such that known quantities of beneficial agent are provided over each corresponding portion of the interventional device.

Figure 13:
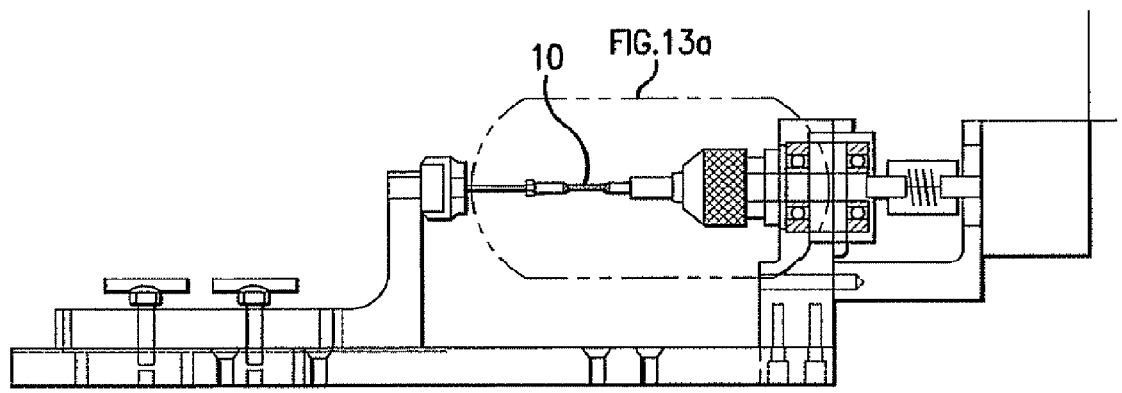
Figure 13A:
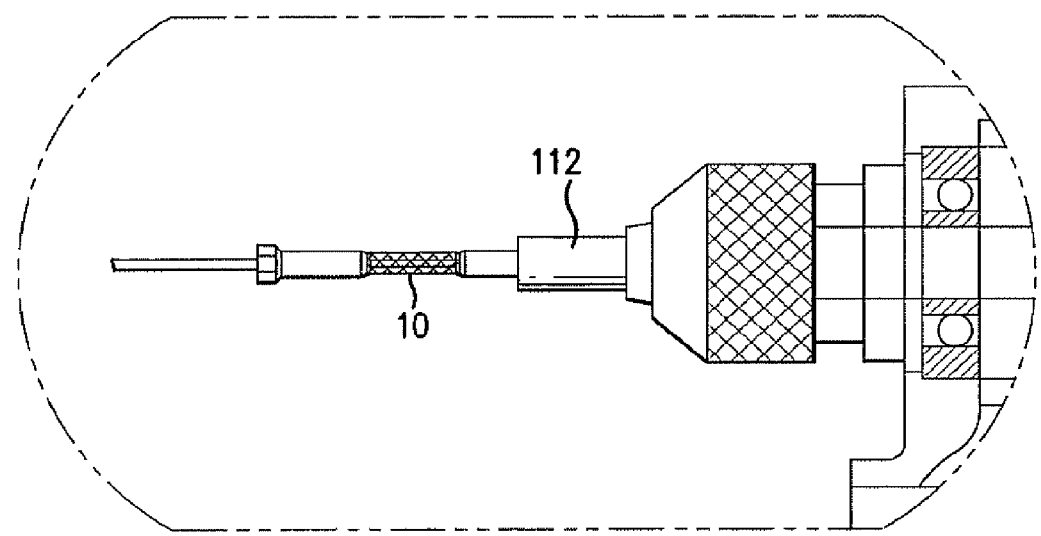

Further in accordance with the invention, a system for loading beneficial agent onto a prosthesis for delivery within a lumen is provided. As shown in FIGS. 7 and 13, the system includes a holder 110 for supporting a prosthesis and a fluid-dispenser having a dispensing element 150 capable of dispensing beneficial agent 15 in discrete droplets 155, each droplet having a controlled trajectory.

The holder includes a mandrel or spindle 112 made of any suitable material known in the art. Preferably, however, the spindle 112 comprises a superelastic material, such as nitinol, or any other material that has shape memory properties. Particularly, manipulation of a stent holder made of stainless steel can result in bending and deformation of the spindle. Such deformation causes poor rotational accuracy and high run-out, e.g., 0.25-2.5 mm, from one end of the spindle to the other end of the spindle. This can cause a lower efficiency of loading beneficial agent onto a prosthesis, and lower efficiency of droplet interaction with the prosthesis because the position of the stent under the jetting head varies as the run out varies. Superelastic materials generally have properties that are able to absorb and recover from up to 8% strain force. Thus, advantageously, nitinol provides a more resilient spindle capable of undergoing repeated manual stent mounting without the plastic deformation that occurs with a stainless steel spindle design.

For purpose of illustration and not limitation, and as shown in FIG. 13, a nitinol spindle 112 may be made using a centerless grinding technique to obtain high concentric accuracy. Despite this grinding process, the centerline of the small diameter part of the spindle (e.g., 0.5 mm diameter) can vary a few degrees from the centerline of the intermediate diameter section (e.g., 2 mm diameter). This variance can be removed by heating the spindle near the junction of the small and intermediate diameter section and bending it to remove most of the residual run out. Upon cooling, the spindle, shown in FIG. 13, assembly retains its new position. The final run out on an exemplary spindle after using these techniques was about 0.051 mm.

The system also includes a driver such as a driver assembly 120 to create relative movement between the holder 110 and the dispensing element 150, and a controller 170 in communication with the driver 120 to define a dispensing path of relative movement between the dispensing element 150 and the holder 110. The controller also communicates with the dispensing element 50 for selectively dispensing beneficial agent in a selected format along the dispensing path onto a selected portion of the prosthesis 10 supported by the holder 10. In one aspect of the invention the holder 110 supporting the prosthesis 10 is moveable while the dispensing element 150 remains stationary during dispensing of beneficial agent 15. However, in another aspect of the invention the holder 110 supporting the prosthesis 10 remains stationary while the dispensing element 150 moves along the dispensing path.

Alternatively, both the holder 110 and dispensing element 150 are moveable. In another aspect of the embodiment, as previously described, the system includes a detector 160 to detect when the dispensing element 150 is aligned with the predetermined portion of the prosthesis 10. Various known components can be used in combination for construction of the system of the present invention. For example, jetLab System II from MicroFab Technologies of Plano, Tex., as modified to include the desired features of the invention can be used.

In yet another embodiment of the invention, a determination of the quantity of beneficial agent dispensed over a given or known surface area can be established. According to one aspect, a predetermined ratio of an identifiable marker is added to the beneficial agent and both the beneficial agent and the marker are loaded onto the prosthesis. Subsequently, the amount of identifiable marker loaded onto the prosthesis is detected to determine the amount of corresponding beneficial agent loaded onto the prosthesis. In one aspect of the invention, the identifiable marker includes radiopaque material. After loading the radiopaque material with the beneficial agent onto the prosthesis, the prosthesis is imaged and an intensity value is measured to determine the amount of beneficial agent loaded thereon and thus local areal density. The identifiable marker in this aspect can also include a fluorescent dye, e.g., coumarin dye. In another aspect of the invention, the identifiable marker includes charged particles, for example and not limitation, protons or electrons. After loading the marker and beneficial agent onto the prosthesis the detecting step includes measuring a charge build-up on or current flow from the prosthesis resulting from the charged particles. The charge build-up or current flow therefore generally corresponds to the amount of beneficial agent loaded onto the prosthesis. Alternatively, because the fluid jetting technology of the present invention is inherently digital, the quantity of beneficial agent dispensed can be determined by counting the droplets that have been jetted or dispersed.

In yet another alternative, the amount of beneficial agent loaded can be measured more generally by weighing the stent before the jetting operation and then after the jetting operation. The weight difference corresponds to the drug loaded with the concentration being a function of the jet flow rate along the length of the stent. Yet another method is to integrate the charge build-up on the prosthesis when a charge-and-deflect system is used. Since each droplet in a charge-and-deflect jetting system has had a surface charge injected onto it to enable the droplet to be deflected in an electrostatic field, either the loss of charge at the charging electrode or the accumulation of charge on the prosthesis can be integrated over time to determine the total volume of fluid that has accumulated on the surface of the device.

Also in accordance with the invention, an on-board spectrometer may be utilized for monitoring the beneficial agent concentration on the jetter reservoirs as a function of time. It is desirable to load beneficial agent such as a drug at a constant concentration. However, due to the evaporation of solvent during the loading process, the concentration of drug will increase. Advantageously, a spectrometer can be configured with a pump to add solvent to the drug such that a constant absorbance on the spectrometer is maintained. The constant absorbance level of the spectrometer is pre-set to monitor an appropriate wavelength. The maintenance of a constant absorbance reading on the spectrometer by the addition of solvent translates to the maintenance of a pre-set drug concentration.

For drop-on-demand jetting systems, this same drug quantification concept can be utilized by adding a constant voltage charging electrode adjacent to the nozzle of the dispenser so as to add a polar charge to each droplet. The coating on the stent, if an insulator, will act as a capacitor to the charge. This detection technique will be able to detect charge build up if a small leakage path is provided or if a second reference surface is provided against which to compare charge build up. Other alternative techniques can be used. For example, if a metal mandrel is present inside the stent it may be used to monitor any lost droplet or splash. The charge that directly transfers to this "electrode" will create an opposite polarity current to the charge presented to the insulated coated surface of the stent.

For each of these detection techniques described above, an appropriate detector can be incorporated in the system of FIG. 7, preferably in communication with controller 170.

In accordance with another aspect of the invention, a second beneficial agent or multiple beneficial agents can be loaded onto the prosthesis as described above. Therefore, further in accordance with the invention, an interventional device comprising a prosthesis loaded with a plurality of discrete droplets of a first beneficial agent and a plurality of discrete droplets of a second beneficial agent is provided, such as by using the system and method shown in FIG. 9.

Particularly, the method described in detail above for one beneficial agent can be modified to allow for loading multiple beneficial agents onto a prosthesis, which might ordinarily lead to undesirable results when using conventional loading techniques. For example and not limitation, the first beneficial agent and the second beneficial agent may have different physical and/or chemical characteristics preventing the beneficial agents from being capable of dissolving in the same solvent, or at the same pH or temperature. In particular, the first beneficial agent can be dissolved in a solvent that is immiscible with the solvent in which the second beneficial agent is dissolved. Alternatively, the first beneficial agent and the second beneficial agent may be incompatible with each other. In particular, the first beneficial agent and the second beneficial agent can be undesirably chemically reactive or may have undesirably different release rates (or contrarily, undesirably similar release rates). Additionally, the first and second beneficial agents can simply be detrimental to each other, e.g., one of the beneficial agents may degrade the efficacy of the other beneficial agent. Thus, although loading the particular multiple beneficial agents onto the same surface of a prosthesis can be desired it often may be problematic due to some incompatibility when using a conventional loading technique. In accordance with the present invention, a method of loading such beneficial agents and an interventional device for the delivery of such beneficial agents is provided.

As noted above, the beneficial agents are loaded in a plurality of discrete droplets on the surface of the prosthesis. The discrete droplets of multiple beneficial agents are preferably loaded onto the prosthesis as unmixed droplets to provide an interspersed pattern or alternatively, the unmixed droplets of beneficial agent can be loaded onto the prosthesis to provide an overlapping pattern of the first beneficial agent and the second beneficial agent. In this manner, the edges of the droplets overlap or alternatively, a larger surface of the droplet overlaps other droplets to provide a layering effect, as depicted in FIG. 10.

Multiple fluid-dispensers are in accordance with the invention, wherein each beneficial agent to be loaded onto the prosthesis is dispensed from a distinct dispensing device. For purpose of illustration and not limitation as shown in FIG. 9, a first dispenser 150 is provided with a first beneficial agent 15' dissolved in a solvent that is compatible for that particular first beneficial agent. Further, a second fluid-dispenser 150" is provided with a second beneficial agent 15" that is different from the first beneficial agent 15', and requiring a different solvent for compatibility. For example, the first beneficial agent could be a water-soluble agent, whereas the second beneficial agent could be a water-insoluble agent, each requiring a different solvent. Accordingly, both beneficial agents are loaded onto the same surface of the prosthesis without problems arising from their immiscibility.

Where two fluid-dispensers are used to load the multiple beneficial agents onto the prosthesis, the trajectories of discrete droplets corresponding to each of the first beneficial agent and the second beneficial agent can be aligned such that the droplets from each beneficial agent combine and mix prior to their being loaded on the prosthesis. In this manner, the first and second beneficial agent can form a third beneficial agent which is loaded onto the prosthesis. For purpose of illustration and not limitation, the first beneficial agent may be bisphenol-A-diglycidyl ether and the second beneficial agent can be triethylenetetramine. Upon combination of the first beneficial agent and the second beneficial agent, a cross linked coating is formed to provide a third beneficial agent. In yet another illustrative example, the first beneficial agent can be bisphenol-A-diglycidyl ether and paclitaxel and the second beneficial agent can be triethylenetetramine. Upon the combination of the two controlled trajectories of beneficial agents, a third beneficial agent is formed, a cross-linked coating entrapping paclitaxel, which is loaded on the prosthesis. Alternatively, the discrete droplets of the first and second beneficial agent can be aligned along trajectories to mix on the surface of the prosthesis.

As noted above, the beneficial agent can include a drug and polymer mixture. In accordance with the method of the invention, the first and second beneficial agents can correspond to drug-polymer mixtures having different concentrations of polymer to effect different release rates of the particular drug in each beneficial agent. For example, the drug-polymer mixture having a higher concentration of polymer would have a slower release of the drug within the lumen than a drug-polymer mixture having a lower concentration. Alternatively, rather than providing drug-polymer mixtures having different polymer concentrations to provide different release rates, it is also possible to dispense beneficial agents using different polymers or other binders, wherein the specific polymer or binder has different diffusivity or affinity to assure delivery of the beneficial agents at different rates. Thus, in accordance with the invention, multiple beneficial agents can be released at rates appropriate for their activities, such that the prosthesis of the invention has multiple beneficial agents which elute off the prosthesis at desired rates.

For example, a cationic phosphorylcholine-linked polymer which has a higher affinity for anionic therapeutic agents can be blended and dispersed as a first beneficial agent and lipophilic phosphorylcholine-linked polymer can be blended with lipophilic drugs as the second beneficial agent to effect different release rates respectively.

In yet another embodiment of the invention, one of the first and second beneficial agents loaded onto the prosthesis can be more hydrophobic or less water-soluble than the other. Thus, in accordance with the invention is provided a prosthesis including first and second beneficial agents wherein one of the beneficial agents is more hydrophobic or less water soluble than the other. In this manner, the more hydrophobic beneficial agent acts as a water barrier or hydration inhibitor for the less hydrophobic beneficial agent, thereby reducing the release rate of the less hydrophobic beneficial agent as disclosed in U.S. Provisional Patent Application 60/453,555 and PCT/US03/07383, each of which was filed on Mar. 10, 2003, and each of which is incorporated herein by reference thereto.

In addition to providing a prosthesis having multiple beneficial agents which are delivered at unique or desired rates, according to another aspect of the invention, the first beneficial agent can be dissolved in solvent wherein the second beneficial agent causes the first beneficial agent to precipitate out of the solvent. For example and not limitation, the first beneficial agent may be rapamycin dissolved in ethanol, and the second beneficial agent may be water. Upon droplet combination using the method and system of the invention, the rapamycin will precipitate within the droplet and be deposited on the prosthesis as a microprecipitate.

In yet another aspect of the invention, at least one of the first and second beneficial agents can be mixed with a binder prior to being loaded onto the prosthesis. Further in accordance with this aspect one of the beneficial agents can be a curative agent for curing the binder on the prosthesis with the beneficial agent mixed therein. For example, see Example 4 below.

As noted above, one of the beneficial agents can be a solvent for the other beneficial agent. Thus, in accordance with the invention, the first beneficial agent, e.g., a drug, polymer, or a combination thereof, can be loaded onto the prosthesis, and subsequently the second beneficial agent, i.e., a solvent, can be loaded onto the prosthesis so as to redistribute the first beneficial agent more uniformly along the prosthesis.

Figure 12:
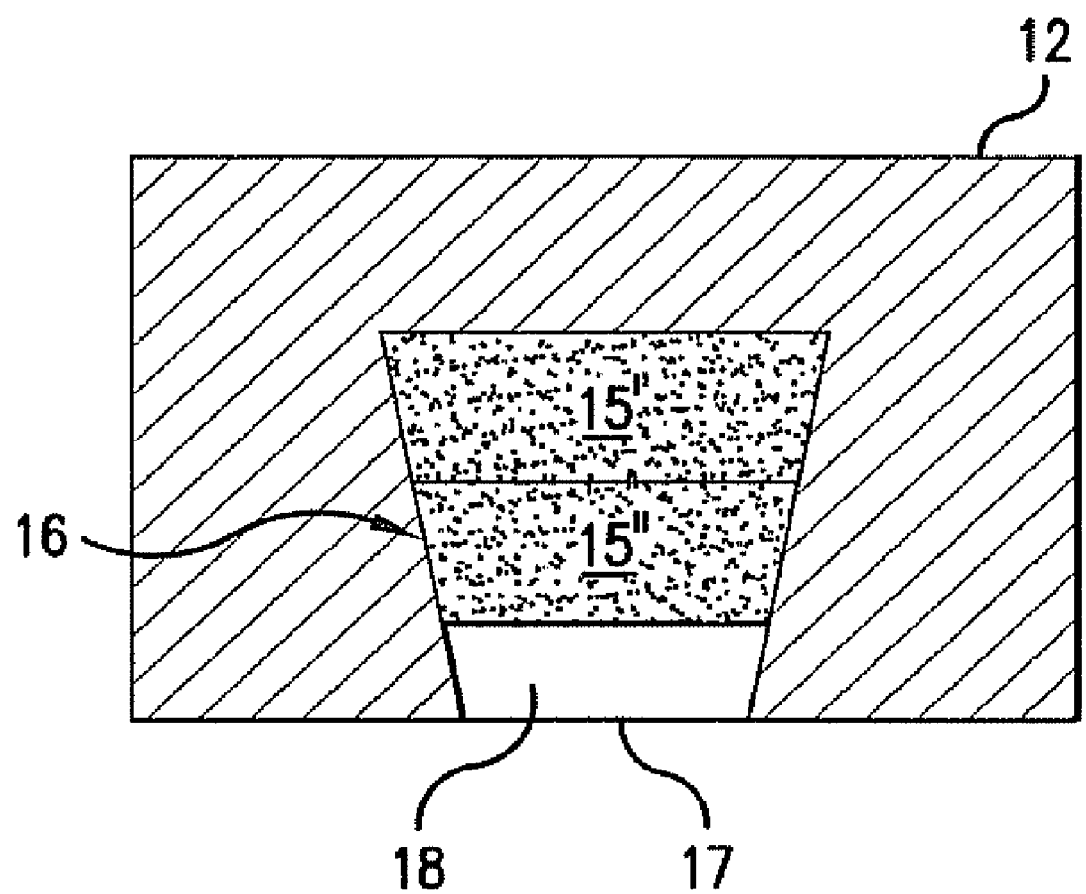

As also noted above, the prosthesis can include at least one reservoir or cavity or trough therein. For purpose of illustration and not limitation, computer controlled profiles of a laser cut stent can be utilized to precisely deposit beneficial agent into the laser cuts on the stent struts. For example, a longitudinal trough can be laser cut, etched, or otherwise formed into the strut, such as in the curve or bend of the strut for instance. In accordance with a preferred aspect of the invention, the cavity or trough is provided with a contoured cross-sectional profile for retention and elution of beneficial agent therein. Particularly, and as depicted schematically in FIG. 12, the cross-sectional profile of the cavity or trough 16 includes a smaller dimension at the interface with the strut surface, so as to define a mouth 17 of the trough 16, and a larger internal cross-dimension of the trough to define a reservoir 18. FIG. 12 shows one such embodiment, wherein mouth 17 is defined for reservoir 18 of trough 16. Use of the fluid jet system and method of the present invention thus allows for beneficial agent to be loaded into the mouth 17 of trough 16, without the entrapment of air within the reservoir 18. An appropriate volume of beneficial agent is deposited in the laser cut profile to at least partially fill the reservoir 18. In this respect, beneficial agent that is deposited in the longitudinal trough can include a combination of drugs or a combination of polymers or a combination of drugs and polymers in different layers.

Furthermore, different layers of polymer and/or drug having different concentrations, or different drug elution rates can be loaded therein. Additionally, an interim polymer and/or final polymer overcoat can be applied over the beneficial agent. Such a deposition configuration in combination with cavities is particularly beneficial for minimizing delamination of the polymer-drug layers, and also provides versatility in controlling drug elution and the generation of various combinations of drug release patterns. A computer profiling approach is also useful to coat drug and polymer layers on the distal and proximal edges of the stent.

In accordance with another aspect of the invention, one or more of the reservoirs or cavities or troughs is loaded with a more hydrophilic first beneficial agent and then a second more hydrophobic beneficial agent is loaded onto the first beneficial agent within the cavity or reservoir in a manner as described above.

Figure 1B:
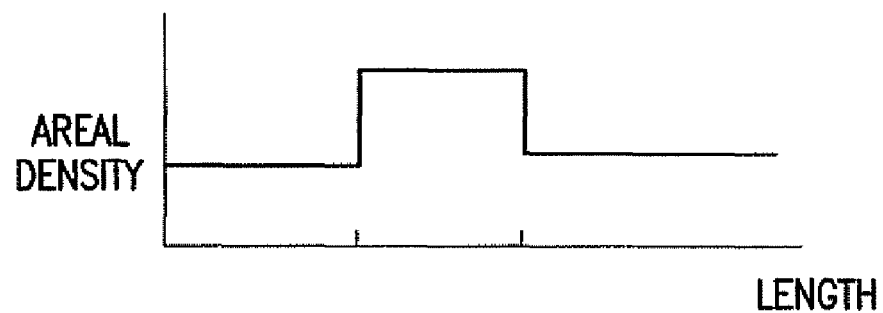
Figure 1C:
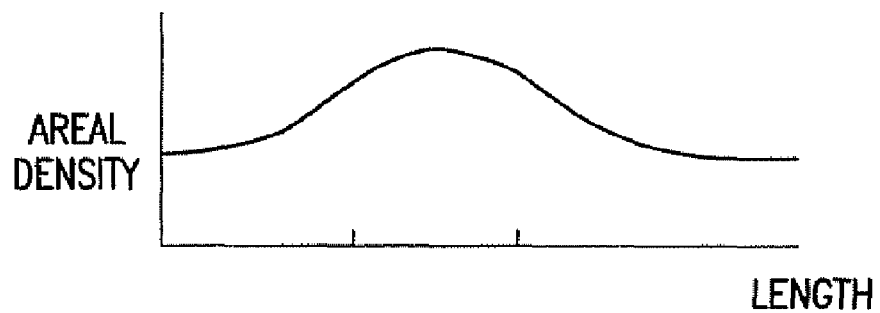

Further in accordance with the invention, using the method and systems described above, a first beneficial agent loaded onto the prosthesis can have a first local areal density and a second beneficial agent loaded onto the prosthesis can have a second local areal density. As used herein, "areal density" refers to the amount of beneficial agent per unit surface area of a selected portion of the prosthesis. "Local areal density" refers to the dosage of beneficial agent per local surface area of the prosthesis The local areal density of the first beneficial agent and the local areal density of the second beneficial agent can be uniform across each respective portion to define stepped changes in local area density as depicted in FIG. 1b or can be varied across a selected portion of the prosthesis to define gradients of local area density, as depicted in FIG. 1c. Accordingly, an interventional device is provided having a prosthesis that is at least partially loaded with beneficial agent having a local areal density that is varied along a selected portion of the body of the prosthesis.

In accordance with a preferred embodiment, the prosthesis has a tubular body when deployed in a lumen. Preferably, the tubular body includes a first and second portion at least partially loaded with beneficial agent such that the first portion has a first local areal density and the second portion has a second local areal density. Each portion may be defined as a preselected length of the prosthesis. Alternatively, as shown in FIG. 1b, the first portion can be defined by a selected set of interconnected structural members and the second portion can be defined as a second set of interconnected members e.g., connectors elements or ring-elements. For example and not limitation, at least one of the first and second set of selected interconnected elements can define at least one ring-shaped element extending around the circumference of the prosthesis.

In another embodiment of the invention, the local areal density is varied as a continuous gradient along a selected portion of the prosthesis as shown in FIG. 1c. Accordingly, in one aspect of the invention the local areal density of beneficial agent is varied such as to provide a prosthesis having a local areal density of beneficial agent at the ends of the prosthesis that is different than the local areal density of beneficial agent at an intermediate section of the prosthesis. For purpose of illustration and not limitation, the local areal density of beneficial agent at the intermediate section of the prosthesis can be greater than that at the proximal and distal ends of the prosthesis as shown in FIG. 1c. Alternatively, the proximal and distal ends of the prosthesis can have a greater local areal density of beneficial agent than that on the intermediate section of the prosthesis. In a preferred embodiment of the invention, the varied local areal density of beneficial agent corresponds to the location of a lesion when the prosthesis is deployed within a lumen. For example, the prosthesis can be loaded to have a greater local areal density of beneficial agent along a preselected portion of the prosthesis that corresponds to the location of the lesion when the prosthesis is deployed in a lumen. Thus, targeted therapy may be achieved with the interventional device of the present invention.

In accordance with the invention, the local areal density can be varied by varying the relative rate in which beneficial agent is loaded to a selected location along the prosthesis. To this end, the frequency in which the droplets of beneficial agent are applied along a unit length of the dispensing path to the prosthesis is varied. Alternatively, the relative rate of loading beneficial agent can be varied by varying the relative movement between the dispensing element and the prosthesis. Another alternative for varying the relative rate of loading beneficial agent is to vary the amount of beneficial agent per droplet dispensed from the dispensing element. Other alternatives for varying the local areal density of beneficial agent loaded onto the prosthesis include mixing the beneficial agent with a binder and varying the ratio of beneficial agent to binder. Alternatively, the amount of the mixture of beneficial agent and binder that is applied to the prosthesis can be varied to achieve a varied local areal density of beneficial agent. Other methods of varying the local areal density of beneficial agent known in the art may be used.

As noted above, the beneficial agent is at least partially loaded onto a surface of the prosthesis. Further in accordance with the invention the prosthesis includes a first surface and a second surface that are at least partially loaded with beneficial agent. In one embodiment of the invention, the first surface and the second surface each correspond to one of the inner surface and the outer surface of the prosthesis. Thus, according to this particular embodiment, beneficial agent, as defined above, is loaded onto the inner or luminal surface of a prosthesis as well as the outer surface of the prosthesis. The method described above can be used for this aspect of the invention, wherein the beneficial agent is loaded on the inner surface of the prosthesis by inserting a fluid dispensing element within the inner diameter of the prosthesis, or by dispensing beneficial agent 15 diametrically across the prosthesis 10 between structural members 12 to impact the inner surface on the opposite side of the prosthesis 10 as shown in FIG. 11. In this regard, the dispensing element 150" is aligned so that the controlled trajectory 152" of discrete droplets 155" of beneficial agent optimally intersect with the inner surfaces of the structural features of the prosthesis 10 and not intersect with the structural features of the outer surface of the prosthesis. For purposes of illustration and not limitation, for a prosthesis comprising an odd number of radial repeats in the pattern of structural features, the preferred alignment of the dispensing element is orthogonal to the central axis of the prosthesis and in a plane that intersects the central axis of the prosthesis. However, for a prosthesis comprising an even number of radial repeats in the pattern of structural features, the preferred alignment of the dispensing element to the prosthesis is orthogonal to the central axis of the prosthesis, but in a plane that does not intersect the central axis of the prosthesis. As another example, for a prosthesis including a tubular member comprising multiple radially and axially repeating structural elements, the preferred alignment of the dispensing element can be determined by assessing the shadow cast by the foreground or outer structural elements on the background or inner structural elements. The preferred plane to align the dispensing element can be determined by assessing the plane in which the maximum amount of unobstructed inner surface is presented upon rotation of the tubular member.

In accordance with this aspect of the invention, the relative motion of the dispensing element and the prosthesis can be coordinated to enable a preprogrammed "raster" image of the position or locations of the structural elements of the inner surface. Alternatively, the vector pattern of the structural elements may be preprogrammed, as previously described. Also, in accordance with the invention, the beneficial agent is dispensed from the dispensing element along a controlled trajectory that is substantially tangential to or near the outer surface of the prosthesis and is loaded on the inner surface of the structural elements of the prosthesis.

In this aspect of the invention, the interventional device can be designed to provide combination therapy of beneficial agents to targeted locations. For example and not limitation, the particular beneficial agent loaded to the luminal or inner surface of the prosthesis can be intended for systemic release, whereas the particular beneficial agent loaded onto the outer surface of the prosthesis is intended for release into the wall of the lumen. In accordance with one aspect of the invention, the beneficial agents loaded onto the luminal side or inner surface of the prosthesis include, without limitation, antiplatelet agents, aspirin, cell adhesion promoters, agents that promote endothelial recovery, agents that promote migration, and estradiol. The beneficial agents loaded onto the outer surface of the prosthesis include without limitation, anti-inflammatories, anti-proliferatives, smooth muscle inhibitors, cell adhesion promoters, and the rapamycin analog ABT-578, i.e., 3S,6R,7E,9R,10R,12R,14S,15E,17E,19E,21S,23S,26R, 27R,34aS)-9,10,12,13,14,21,22,23,24,25,26,27,32,33,34, 34a-Hexadecahydro-9,27-dihydroxy-3-[(1R)-2-[(1S,3R, 4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1, 5,11,28,29(4H,6H,31H)-pentone; 23,27-Epoxy-3H-pyrido [2,1-c][1,4]oxaazacyclohentriacontine-1,5,11,28,29(4H,6H, 3H)-pentone In accordance with another embodiment of the invention, the first surface of the prosthesis is defined by a plurality of interconnecting structural members. Accordingly, the first surface can include a first selected set of structural members, e.g., a connector member, and the second surface can include a second selected set of the structural members, e.g., a ring-shaped element extending around the circumference of the prosthesis.

As noted above, the beneficial agent is loaded onto the prosthesis to provide a controlled local areal density across a length of the interventional device. That is, it may be desirable to provide a greater concentration of beneficial agent at one portion of a prosthesis and a lower concentration, or perhaps no beneficial agent, at another portion of the prosthesis. For example, in one embodiment, a greater local areal density can be provided at a first portion, e.g., intermediate portion 10b, of a stent 10, as shown in FIG. 1a, while providing a lower local areal density of beneficial agent to a second portion, e.g., one or both end portions (10a, 10c), of the stent 10. In accordance with the present invention, each of the first and second portions of the prosthesis may be defined by any of a variety of patterns or selected portions of the prosthesis. For example, the first portion of the prosthesis can be defined by longitudinal connectors whereas the second portion of the stent is defined by annular rings, or vice versa, as illustrated in FIG. 6.

Figure 2:
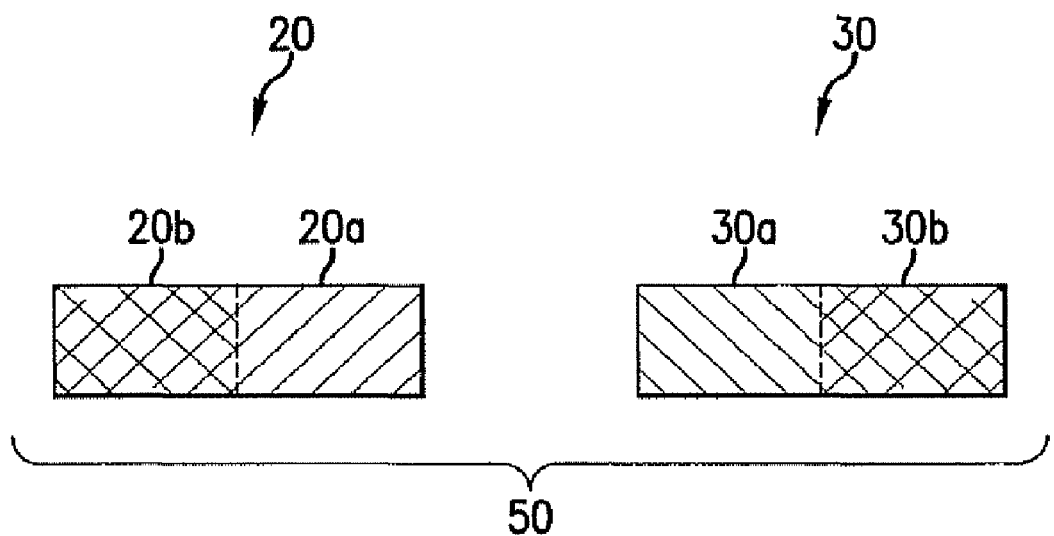
Figure 3:
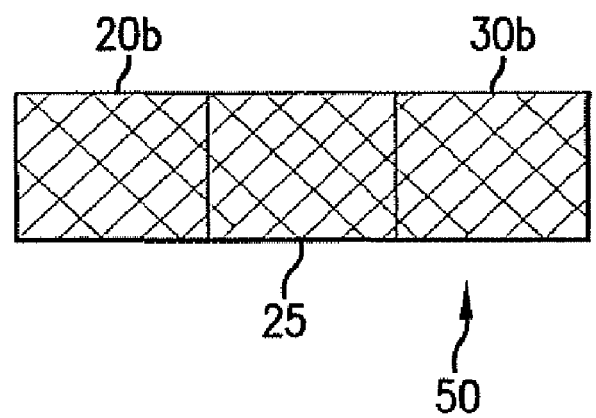

In accordance with another aspect of the present invention, the interventional device includes a first prosthesis and a second prosthesis in combination to define an overlapping portion and at least one non-overlapping portion. For example, and as embodied herein, FIG. 2 or 3 present a schematic representation of a nested interventional device including a first prosthesis 20 and a second prosthesis 30 configured to be deployed in an overlapping relationship. The interventional device, however, can optionally include more than two prostheses in combination, if desired. Such interventional devices 50 include but are not limited to nested stents and modular bifurcated stents. For purpose of illustration and not limitation, FIG. 2 shows a first prosthesis 20 having a first portion 20a and a second portion 20b and a second prosthesis 30 having a first portion 30a and a second portion 30b. As shown schematically, the beneficial agent distribution profile includes a first local areal density of beneficial agent on one of the first and second portions of one or both of the first prosthesis and the second prosthesis. For example and not by limitation, the first portion 20a of the first prosthesis 20 has half the local areal density of beneficial agent as compared to the second portion 20b of the first prosthesis 20. The first portion 30a of the second prosthesis 30, likewise, has half the local areal density of beneficial agent compared to the second portion 30b of the second prosthesis 30. In this manner, when the ends of two stents are superimposed or deployed in an overlapping relationship 25 during a procedure, the local areal density of beneficial agent along the interventional device 50 is controlled so as to be uniform. If desired, alternative concentrations can be provided on each portion so as to provide the desired effect in combination.

In accordance with the invention, as shown in FIG. 3, a controlled local areal density of beneficial agent is thus provided across a length of the interventional device 50 upon combination of the first prosthesis having first portion 20a and second portion 20b with the second prosthesis having first portion 30a and second portion 30b, as shown in FIG. 2. In particular, as shown in FIG. 3, the overlapping segment 25 of first prosthesis 20 and the second prosthesis 30 has an equal local areal density of beneficial agent as compared to non-overlapping segments 20b and 30b.

Alternatively, the beneficial agent distribution profile for the interventional device may be controlled to include any of a variety of desired patterns. For example, the interventional device can have a decreased local areal density of beneficial agent on the distal and proximal ends of each prosthesis body, as noted above. This profile is highly desirable in preventing adverse dosing of beneficial agent if multiple prostheses are placed in combination with each other but still provides for decreased dosage of the extreme ends of the interventional device as a whole. Alternatively, as embodied herein, the beneficial agent distribution profile can provide a controlled local areal density that is uniform along the length of first prosthesis and second prosthesis in combination, or multiple prostheses in combination. Alternatively, in accordance with the invention, the beneficial agent distribution profile provides a controlled local areal density that is varied along the length of the first prosthesis and the second prosthesis in combination, or multiple prostheses in combination.

For illustration purposes, overlapping or nested prostheses, as shown in FIG. 3, can have beneficial agent distribution profiles such that the controlled local areal density of beneficial agent of a non-overlapping segment is in fact greater than the controlled local areal density of beneficial agent of a overlapping segment. Similarly, the alternative can also be true; that a overlapping segment is controlled to have a greater or different local areal density of beneficial agent than a non-overlapping segment. Advantageously, this feature also enables selective dosing of beneficial agent to a targeted area when using multiple prostheses in combination, as well as a single prosthesis alone, Selective dosing of beneficial agent to a targeted area means that the beneficial agent can be applied to the prosthesis or prostheses in combination such that the desired beneficial agent is loaded onto the prosthesis in a selective pattern so that the beneficial agent or beneficial agents are released from the prosthesis in close proximity to a targeted location, Fluid jetting as previously described is particularly preferred for selective dosing.

Figure 4:
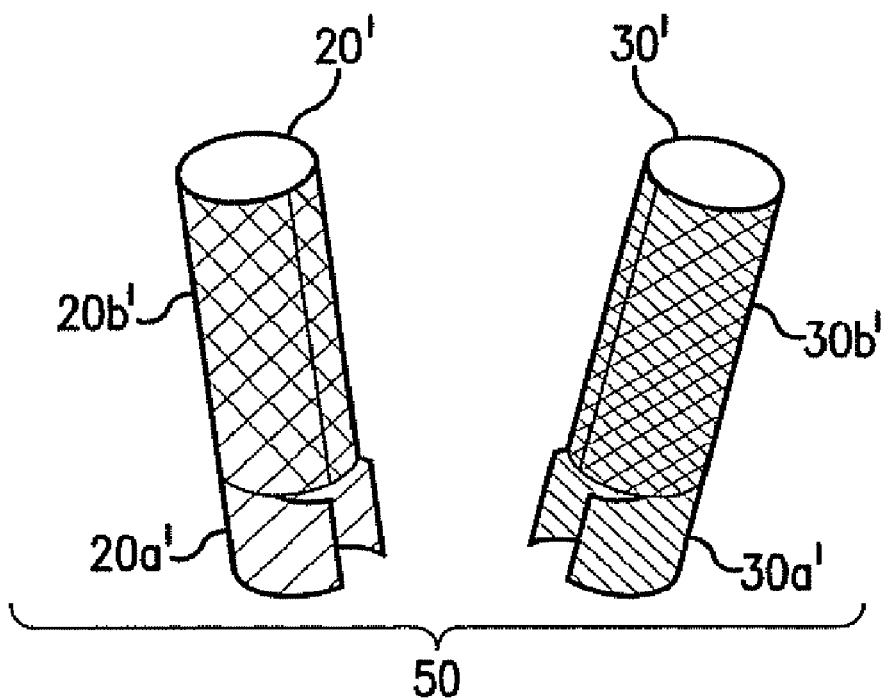
Figure 5:
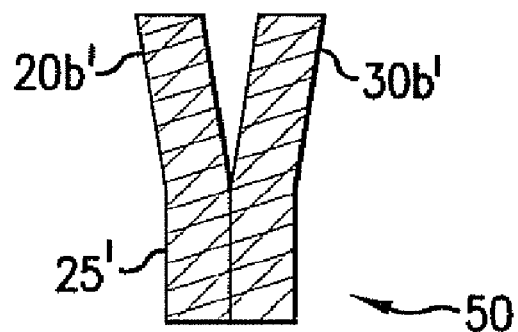

In accordance with the present invention, and as embodied schematically in FIG. 5, a bifurcated interventional device also can be provided, which includes a first prosthesis 20' and a second prosthesis 30' in combination to define an overlapping portion 50' and non overlapping portions 20b', 30b'. For purposes of illustration and not limitation, FIG. 4 shows a first prosthesis 20' having a first portion 20a' and a second portion 20b', and a second prosthesis 30' having a first portion 30a' and a second portion 30b'. As shown for purpose of illustration and not limitation, the beneficial agent distribution profile includes a first local areal density of beneficial agent on one of the first and second portions of one or both of the first prosthesis 20' and the second prosthesis 30'. For example, and not by limitation, the first portion 20a' of the first prosthesis 20' has half the local areal density of beneficial agent as compared to the second portion 20b' of the first prosthesis. The first portion 30a' of the second prosthesis 30' has half the local areal density of the second portion 30b' of the second prosthesis 30'. In accordance with the present invention, as shown in FIG. 5, a controlled local areal density of beneficial agent is thus provided across a length of the bifurcated interventional device 50 upon combination of the first prosthesis having first portion 20a' and second portion 20b' with the second prosthesis having first portion 30a' and second portion 30b', as shown in FIG. 4.

Another feature of the present invention includes applying a layer of base material on a selected portion of the prosthesis described above. The beneficial agent is loaded onto the base material layer according to the methods described above. The base material layer preferably defines a pattern for loading the beneficial agent onto the prosthesis.

The present invention also encompasses, for any of the embodiments disclosed, the application of a rate-controlling topcoat over the beneficial agent loaded prosthesis for further controlling or sustaining the release of beneficial agent. The rate-controlling topcoat may be added by applying a coating layer posited over the beneficial agent loaded prosthesis. The thickness of the layer is selected to provide such control. Preferably, the overcoat is applied by fluid-jet technology. Advantageously, fluid jetting an overcoat such as a polymer overcoat allows a thinner and more uniform layers. However other conventional methods can be used such as other fluid-dispensers, vapor deposition, plasma deposition, spraying, or dipping, or any other coating technique known in the art.

The present invention also provides a method for manufacturing an interventional device for delivery of beneficial agent. This method comprises the steps of providing a first prosthesis to be deployed within a lumen; providing a second prosthesis configured to be deployed in an overlapping relationship with the first prosthesis, the first prosthesis and the second prosthesis in combination defining at least one non-overlapping segment and an overlapping segment; and loading the first prosthesis and the second prosthesis with beneficial agent to provide a controlled local areal density along a length of the first prosthesis and the second prosthesis in combination. The method described in detail above is preferred for such loading step.

The present invention also provides a method of delivering beneficial agent. In accordance with this method, as described in detail in conjunction with the description of the interventional device of the present invention above, the method comprising the steps of providing a first prosthesis having a tubular body when deployed in a lumen; providing a second prosthesis having a tubular body when deployed in a lumen; loading at least one of the first prosthesis and the second prosthesis with beneficial agent; deploying the first prosthesis into a lumen; deploying the second prosthesis into the lumen to define in combination with the first prosthesis at least one non-overlapping segment and an overlapping segment; wherein the beneficial agent is loaded onto at least one of the first prosthesis and the second prosthesis to provide a controlled local areal density of beneficial agent across a length of the first prosthesis and the second prosthesis when deployed. The method described in detail above is preferred for such loading step.

The present invention will be further understood by the examples set forth below, which are provided for purpose of illustration and not limitation.

EXAMPLES

Example 1

Jetting of Reactive Substances

The components of a commercial two-part epoxy formulation are mixed by the jetting process and applied to a surface to form a coating. In a formulation manufactured by Buehler, Lake Bluff Ill., one part is a liquid "epoxide resin" that contains 4,4' isopropylidenediphenol epichlorohydrin resin and butyl glycidyl ether. The second part is a liquid "hardener" that contains diethylene triamine, triethylene tetramine, and polyoxypropylenediamine. In the jetting process, one reagent jet system (A) is loaded with epoxide resin and a second jetting system (B) is loaded with hardener. The jets are aligned such that the droplets emanating from each jet combine in midair and travel to the target device to form a crosslinked coating, after a curing time of 2-8 hours. The volume of a droplet emanating from jet A is 5 times larger than the volume of a droplet emanating from Jet B and the total number of droplets dispensed from each jet are approximately equal.

Example 2

Jetting of Reactive Substances

The components of a commercial two-part epoxy formulation are mixed by the jetting process and applied to a surface to form a coating. In a two part commercial formulation manufactured by Buehler, Lake Bluff Ill., one part is a liquid "epoxide resin" which contains 4,4' isopropylidenediphenol epichlorohydrin resin and butyl glycidyl ether. The second part is a liquid "hardener" that contains diethylene triamine, triethylene tetramine, and polyoxypropylenediamine. In the jetting process, one reagent jet system (A) is loaded with epoxide resin and a second jetting system (B) is loaded with hardener. The jets are aligned such that the droplets emanating from each jet combine in midair and travel to the target device to form a crosslinked coating, after a curing time of 2-8 hours. The volume of a droplet emanating from jet A is 4 times larger than the volume of a droplet emanating from Jet B and the total number of droplets dispensed from each jet are approximately equal. This coating cures at a faster rate than the coating described in example 1.

Example 3

Jetting of Reactive Substances

The components of a commercial two-part epoxy formulation are mixed by the jetting process and applied to a surface to form a coating. In a two part commercial formulation manufactured by Buehler, Lake Bluff Ill., one part is a liquid "epoxide resin" which contains 4,4' isopropylidenediphenol epichlorohydrin resin and butyl glycidyl ether. The second part is a liquid "hardener" that contains diethylene triamine, triethylene tetramine, and polyoxypropylenediamine. In the jetting process, one reagent jet system (A) is loaded with epoxide resin and a second jetting system (B) is loaded with hardener. The jets are aligned such that the droplets emanating from each jet combine in midair and travel to the target device to form a crosslinked coating, after a curing time of 2-8 hours. The volume of a droplet emanating from jet A is approximately equal to the volume of a droplet emanating from Jet B, but the total number of droplets dispensed from jet A is 4 times more than from jet B.

Example 4

Formation of a Crosslinked Network Containing Biologically Active Agents

One reagent jet system (A) is loaded with a liquid epoxide resin and a solubilized formulation of the drug, paclitaxel, 20% by weight with respect to the epoxide resin. A second jetting system (B) is loaded with hardener similar to that described in example 1 combined with an equal weight or less of a biocompatible polymer. One example of such a species is a phosphorylcholine linked polymer of the general formula poly($MPC_w:LMA_x:HPMA_y:TSMA_z$), where MPC is 2-methacryoyloxyethylphosphorylcholine, LMA is lauryl methacrylate, HPMA is hydroxypropyl methacrylate and TSMA is trimethoxysilylpropyl methacrylate. This polymer is dissolved in a solvent such as chloroform. The jets are aligned such that the droplets from each jet combine in midair and travel to the target device to form a crosslinked coating entrapping the drug and polymer. The volume of a droplet emanating from jet A is 5 times larger than the volume of a droplet emanating from jet B and the total number of droplets dispensed from each jet are approximately equal. The coating is heated for 4 hours at 70 degrees C. to cause crosslinking of the phosphorylcholine-linked polymer predominantly with itself by means of the trimethoxysilane groups, and simultaneously accelerating the curing of the epoxide resin with the hardener.

Example 5

Formation of a Drug Microprecipate

One reagent jet system (A) is loaded with rapamycin dissolved in ethanol. A second jetting system is loaded with water. The droplet volume of one drop emanating from jet A is 50 picoliters and the droplet volume of one drop emanating from Jet B is 150 picoliters. The jets are aligned such that the droplets from each jet combine in midair and travel to the target device. During the droplet combination the rapamycin will precipitate within the droplet and be deposited on the target surface as a microprecipitate.

Example 6

Loading of Drug onto a Polymer Base-Coated Coronary Stent

In a demonstration of feasibility, a stock jetting solution of 20 mg/ml ABT-578+4 mg/ml phosphorylcholine-linked methacrylate polymer (PC) in isobutanol was prepared. A fluid jetting system manufactured by MicroFab Technologies of Plano, Tex. was programmed to jet 75 micrograms of drug evenly over a 1.4×11 mm OC BiodivYsio stent to obtain an areal density of 5 micrograms per linear mm. Jetting of 21,888 drops into a vial containing 10 ml of isobutanol gave 77 micrograms of ABT-578 as determined spectrophotometrically at 278 nm. Under these conditions, 1 drop was 170-180 picoliters and had a diameter between 67 and 70 microns. The stent contained a base coating of phosphorylcholine-linked methacrylate polymer (PC). It was mounted on a fixture that included a mandrel that provided for controlled rotation ($\theta$) about a central axis coaxial with the stent and a stage that provided for lateral movement (X) along the axis of the stent. The motion control was set up to rotate the stent a total of 720 degrees. A view orthogonal to the axis of the rotating stent showed two possible tangential off-axis positions, approximately 50 microns inside a point tangent to the outer surface of the stent, one on each side of the rotation centerline, that provided relatively few instances where a jet trajectory would not impinge on at least one stent structural element. One of these off-axis positions was first selected to start the drug loading. A mandrel mounted stent was positioned so that the trajectory of jetted droplets would impinge on the stent struts at this "off-axis" location. The motion controller was set up to move the stent axially in the X direction and began its motion at a position where the jet trajectory was off the end of the stent. The motion controller ramped up to a predetermined velocity and turned on the fluid jetting head as soon as motion along the X axis reached constant velocity and the end of the stent struts were in a position directly under the jet head. Every time the stent passed completely under the jet head along this off-axis path in the X direction, the motion controller would then ramp down the velocity, stop and rotate the stent 5 degrees. The linear direction was reversed and the next pass was made. After 360 degrees was reached, (72 passes) the table was translated approximately a distance equal to the internal diameter of the stent (1 ID) to the other off-axis position and 72 more passes were made for an additional rotation of 360 degrees. Each stent was thus jetted twice to obtain its drug loading.

Seven (7) stents were loaded with drug. Observation of drug-loaded stents under a stereomicroscope indicated that no webbing occurred between stent struts and the surfaces were cosmetically smooth. The stents were subsequently extracted into isobutanol for measurement of the drug obtained and the results are shown below.

| Stent | ABT-578 (micrograms) |
| --- | --- |
| 1 | 70 |
| 2 | 72 |
| 3 | 69 |
| 4 | 69 |
| 5 | 53 |
| 6 | 61 |
| 7 | 60 |

The average loading obtained was 65 micrograms. The calculated capture efficiency was 84% based on the number of counted droplets of drug dispensed.

Example 7

Loading of PC-Coated Peripheral Stents by Reagent Jetting

In a similar feasibility demonstration experiment, a fluid jetting system manufactured by MicroFab Technologies of Plano, Tex. was programmed to dispense 59,904 drops, approximately 3× that used for the 11 mm OC stent. These peripheral vascular stents (SFA) were 5×30 mm and were mounted on a larger sized rotation fixture. The stent matrix was much more open than seen on the OC coronary stent; however, good capture efficiency was obtained.

| Stent | ABT-578 (micrograms) |
|---|---|
| 1 | 187 |
| 2 | 176 |
| 3 | 185 |
| average | 183 Avg. |

The jetter dispensed 211 micrograms of drug per stent, having a capture efficiency of 86%.

Example 8

Overcoating of a Drug-Loaded Stent with Polymer

A 10 mg/ml solution of phosphorylcholine-linked methacrylate polymer (PC) was made in isobutanol. A total of 288 passes along the axial dimension of the stent and over 1440 degrees of rotation under the conditions used in previous examples, produced an overcoat at 5 micrograms per linear mm.

Example 9

Overcoating of a Drug-Loaded Stent with Polymer having a Variable Areal Density

A 10 mg/ml solution of phosphorylcholine-linked methacrylate polymer (PC) is made in isobutanol. The linear travel speed of the stent under the jet head is programmed to be 50% slower during the beginning 25% of the stent length and the ending 25% of length. The jetting rate is not varied over the length of the stent. A total of 288 passes along the axial dimension of the stent and over 1440 degrees of rotation are made. Under these conditions, the stent obtains an increased amount of PC on both ends of the stent compared to the middle regions.

Example 10

Drug-Loaded Stent having a Variable Areal Density of Drug

A stock jetting solution of 20 mg/ml ABT-578+4 mg/ml phosphorylcholine-linked methacrylate polymer (PC) in isobutanol is prepared. The linear travel speed of the stent under the jet head is programmed to be 50% faster during the beginning 25% of the stent length and the ending 25% of length. The jetting rate is not varied over the length of the stent. A total of 144 passes along the axial dimension of the stent and over 720 degrees of rotation are made. Under these conditions, the stent obtains a decreased amount of ABT-578 on both ends of the stent compared to the middle regions.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. For example, a charge-and-deflect dispenser can be replaced with a drop-on-demand fluid jetter, or vice versa. Such changes and modifications, including without limitation those relating to the chemical structures, substituents, derivatives, intermediates, syntheses, formulations and or methods of use of the invention, can be made without departing from the spirit and scope thereof.

What is claimed is:

1. A system for loading beneficial agent onto a prosthesis for delivery within a lumen, the system comprising:
    a holder for supporting a prosthesis to be deployed within a lumen;
    a fluid-dispenser having a dispensing element capable of dispensing beneficial agent in discrete droplets, each droplet having a controlled trajectory, the dispensing element and the holder being movable relative to each other, said dispensing element being positioned at a distance sufficient such that the dispensing element and prosthesis on the holder are separated by a distance that avoids simultaneous contact of the dispensing element and prosthesis by a discrete droplet;
    a driver for creating relative movement between the dispensing element and the holder;
    a controller in communication with the driver to define a dispensing path for dispensing discrete droplets of beneficial agent with the controlled trajectory in a raster format, the controller also in communication with the dispensing element to selectively dispense beneficial agent from the dispensing element to a portion of the prosthesis supported by the holder along the dispensing path; and
    an optical detector configured to detect when the dispensing element is aligned with the portion of the prosthesis supported by the holder.

2. The system of claim 1, wherein the holder includes a spindle made of a superelastic material.

3. The system of claim 1, wherein the controller is programmed with the portion of the prosthesis to which beneficial agent is to be dispensed.

4. The system of claim 1, further comprising an identifiable marker configured to be loaded onto the prosthesis, wherein said beneficial agent detector in communication with the controller configured to determine the amount of beneficial agent loaded on the prosthesis detects the identifiable marker.

5. The system of claim 1, wherein the controller is configured to instruct dispensing of the beneficial agent onto the prosthesis until the loaded amount of beneficial agent matches a predetermined amount of beneficial agent.

6. The system of claim 1, further comprising:
    a beneficial agent detector in communication with the controller configured to determine an amount of beneficial agent loaded on the prosthesis, the beneficial agent detector being configured to be capable of detecting the number of discrete droplets dispensed from the fluid-dispenser onto the prosthesis to determine a corresponding amount of beneficial agent loaded to the prosthesis.

7. The system of claim 1, wherein the optical detector is a linear array detector.

8. The system of claim 7, wherein the linear array detector has a resolution corresponding to the size of discrete droplets dispensed by the fluid-dispenser.

9. The system of claim 1, wherein the optical detector is an infrared detector.

10. The system of claim 1, wherein the optical detector is configured to detect the presence of the portion of the prosthesis that is about to be moved by the driver and holder into a position in front of the fluid-dispenser.

11. The system of claim 1, wherein the optical detector is configured to detect a shadow cast by the portion of the prosthesis.

12. The system of claim 1, further comprising a beneficial agent detector in communication with the controller configured to determine an amount of beneficial agent loaded on the prosthesis, the beneficial agent detector being configured to measure an intensity of radiopaque material.

13. The system of claim 1, further comprising a beneficial agent detector in communication with the controller configured to determine an amount of beneficial agent loaded on the prosthesis, the beneficial agent detector being configured to be capable of detecting charge build-up on or current flow from the prosthesis to determine a corresponding amount of beneficial agent loaded to the prosthesis.

14. The system of claim 13, further comprising a charging electrode adjacent the fluid-dispenser configured to add a charge to the discrete droplets.

15. The system of claim 1, wherein the controller is not preprogrammed with a map of the portion of the prosthesis to which beneficial agent is to be dispensed.

16. The system of claim 1, wherein the prosthesis is a stent and the portion of the prosthesis is a structural strut of the stent.

* * * * *